(12) United States Patent
Schwarz et al.

(10) Patent No.: US 7,670,991 B2
(45) Date of Patent: Mar. 2, 2010

(54) SUBSTITUTED BENZOYLCYCLOHEXENONES AND THEIR USE AS HERBICIDAL AGENTS

(75) Inventors: Hans-Georg Schwarz, Langenfeld (DE); Klaus-Helmut Muller, Dusseldorf (DE); Stefan Herrmann, Langenfeld (DE); Dorothee Hoischen, Dusseldorf (DE); Kristian Kather, Langenfeld (DE); Stefan Lehr, Liederbach (DE); Otto Schallner, Monheim (DE); Mark Wilhelm Drewes, Langenfeld (DE); Peter Dahmen, Neuss (DE); Dieter Feucht, Monheim (DE); Rolf Pontzen, Leichlingen (DE); Shinichi Narabu, Yuki (JP); Akihiko Yanagi, Oyama (JP); Shinichi Shirakura, Oyama (JP); Toshio Goto, Kokubunji-machi (JP); Yoshihiro Yamaguchi, Oyama (JP)

(73) Assignee: Bayer CropScience AG, Monheim (DE)

( * ) Notice: Subject to any disclaimer, the term of this patent is extended or adjusted under 35 U.S.C. 154(b) by 1272 days.

(21) Appl. No.: 10/477,817

(22) PCT Filed: May 3, 2002

(86) PCT No.: PCT/EP02/04851

§ 371 (c)(1),
(2), (4) Date: Apr. 9, 2004

(87) PCT Pub. No.: WO02/092574

PCT Pub. Date: Nov. 21, 2002

(65) Prior Publication Data

US 2004/0171491 A1    Sep. 2, 2004

(30) Foreign Application Priority Data

May 16, 2001 (DE) .................... 101 23 887
Aug. 6, 2001 (DE) .................... 101 38 576

(51) Int. Cl.
*C07D 239/04* (2006.01)
*A01N 43/00* (2006.01)

(52) U.S. Cl. .............. 504/242; 549/487; 549/488; 549/493; 549/496; 549/473

(58) Field of Classification Search ............. 548/300.1; 504/280, 242; 549/473, 487, 488, 493, 496
See application file for complete search history.

(56) References Cited

U.S. PATENT DOCUMENTS

| 4,780,127 A | 10/1988 | Michaely et al. ............. 71/103 |
| 4,806,146 A | 2/1989 | Carter .......................... 71/98 |
| 4,816,066 A | 3/1989 | Michaely et al. ............. 71/123 |
| 4,946,981 A | 8/1990 | Carter et al. .................. 558/415 |
| 5,006,158 A | 4/1991 | Carter et al. .................. 71/98 |
| 5,085,688 A | 2/1992 | Michaely et al. ............. 71/103 |
| 5,110,343 A | 5/1992 | Ueda et al. .................... 71/88 |
| 6,004,903 A | 12/1999 | von Deyn et al. ............. 504/239 |
| 6,153,759 A | 11/2000 | von Deyn et al. ............. 548/131 |
| 6,376,429 B1 | 4/2002 | Van Almsick et al. ....... 504/271 |
| 6,432,881 B1 | 8/2002 | Engel et al. ................... 504/280 |
| 6,559,100 B1 | 5/2003 | Engel et al. ................... 504/223 |
| 6,924,251 B1 | 8/2005 | Schwarz et al. |

FOREIGN PATENT DOCUMENTS

| EP | 186 119 | 8/1989 |
| JP | 11-292849 | 10/1999 |
| WO | 97/46530 | 12/1997 |

*Primary Examiner*—Sabiha Qazi
(74) *Attorney, Agent, or Firm*—Richard E. L. Henderson

(57) ABSTRACT

The invention relates to novel substituted benzoylcyclohexenones of the formula (I)

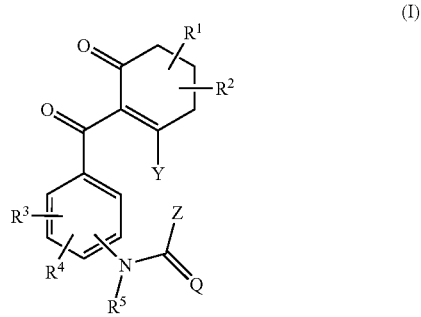

in which Q, $R^1$, $R^2$, $R^3$, $R^4$, $R^5$, Y and Z have one of the meanings given in the disclosure, to processes for their preparation, and to their use.

8 Claims, No Drawings

SUBSTITUTED BENZOYLCYCLOHEXENONES AND THEIR USE AS HERBICIDAL AGENTS

The present patent application claims the right of priority under 35 U.S.C. 119 and 35 U.S.C. 365 of International Application PCT/EP02/04851, filed May 3, 2002, which was published in German as International Patent Publication WO 02/092,574 on Nov. 21, 2002, which is entitled to the right of priority of German Patent Applications 101 23 887.9, filed May 16, 2001, and 101 38576.5, filed Aug. 6, 2001.

The invention relates to novel substituted benzoylcyclohexenones, to processes for their preparation and to their use as herbicides.

It is already known that certain substituted benzoylcyclohexenones or benzoylcyclohexanediones, such as, for example, the compounds N-[2,6-dichloro-3-[(3,3-dimethyl-2,6-dioxo-cyclohexyl)-carbonyl]-phenyl]-acetamide, N-[2-chloro-3-[(2,6-dioxo-cyclohexyl)-carbonyl]-4-nitro-phenyl]-acetamide, N-[2-chloro-3-[(2,6-dioxo-cyclohexyl)-carbonyl]-phenyl]-acetamide, N-[2,6-dichloro-3-[(2,6-dioxo-cyclohexyl)-carbonyl]-phenyl]-acetamide (cf. U.S. Pat. No. 4,780,127), have herbicidal properties (cf. also EP-A-090 262, EP-A-135 191, EP-A-137 963, EP-A-186-118, EP-A-186 119, EP-A-186 120, EP-A-319 075, WO-A-96/26200, WO-A-97/46530, WO-A-99/07688, WO-A-99/10327, WO-A-00/05221, WO-A-00/21924). However, the activity of these compounds is not entirely satisfactory.

This invention now provides novel substituted benzoylcyclohexenones of the general formula (I)

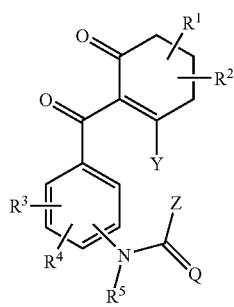

(I)

in which

Q represents O (oxygen) or S (sulphur), $R^1$ represents hydrogen, halogen or in each case optionally substituted alkyl, alkylthio or aryl, $R^2$ represents hydrogen, halogen or optionally substituted alkyl, or together with $R^1$ represents O (oxygen) or alkanediyl (alkylene), $R^3$ represents hydrogen, nitro, cyano, carboxyl, carbamoyl, thiocarbamoyl, halogen, or in each case optionally substituted alkyl, alkoxy, alkylthio, alkylsulphinyl, alkylsulphonyl, alkylamino, dialkylamino, dialkylaminocarbonyl or dialkylaminosulphonyl, $R^4$ represents hydrogen, nitro, cyano, carboxyl, carbamoyl, thiocarbamoyl, halogen, or in each case optionally substituted alkyl, alkoxy, alkylthio, alkylsulphinyl, alkylsulphonyl, alkylamino, dialkylamino, dialkylaminocarbonyl or dialkylaminosulphonyl, $R^5$ represents hydrogen or in each case optionally substituted alkyl, alkoxy, alkylthio, alkylsulphinyl, alkylsulphonyl, alkenyl, alkinyl, cycloalkyl, cycloalkylalkyl, aryl, arylthio, arylsulphinyl, arylsulphonyl, arylalkyl, or represents the grouping —C(Q)-Z, Y represents hydroxyl, halogen or in each case optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkinyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl, and Z represents hydrogen, amino, cyanoamino, nitroamino, hydroxyamino, hydrazino, or represents in each case optionally substituted alkyl, alkylcarbonyl, alkoxy, alkoxycarbonyl, alkylthio, alkylamino, alkoxyamino, alkylhydrazino, alkylcarbonylhydrazino, alkoxycarbonylhydrazino, alkylsulphonylhydrazino, dialkylamino, N-alkyl-alkoxyamino, dialkylhydrazino, alkenyl, alkenyloxy, alkenylamino, alkenyloxyamino, alkinyl, alkinyloxy, alkinylamino, cycloalkyl, cycloalkyloxy, cycloalkylamino, cycloalkylhydrazino, cycloalkylalkyl, cycloalkylalkoxy, cycloalkylalkylamino, aryl, arylcarbonyl, aryloxy, aryloxycarbonyl, arylthio, arylamino, arylhydrazino, arylalkyl, arylalkoxy, arylalkylthio, arylalkylamino, heterocyclyl, heterocyclyloxy, heterocyclylthio, heterocyclylamino, the grouping —N=(heterocyclyl), heterocyclylalkyl, heterocyclylalkoxy, heterocyclylalkylthio or heterocyclylalkylamino, including all possible tautomeric forms of the compounds of the general formula (I) and the possible salts of the compounds of the general formula (I)

where the radicals $R^3$ and $R^4$ are preferably located in position (2) and (4), respectively, of the phenyl ring and where the abovementioned compounds N-[2,6-dichloro-3-[(3,3-dimethyl-2,6-dioxo-cyclohexyl)-carbonyl]-phenyl-acetamide, N-[2-chloro-3-[(2,6-dioxo-cyclohexyl)-carbonyl]-4-nitro-phenyl]-acetamide and N-[2-chloro-3-[(2,6-dioxo-cyclohexyl)-carbonyl]-phenyl]-acetamide and N-[2,6-dichloro-3-[(2,6-dioxo-cyclohexyl)-carbonyl]-phenyl-acetamide which are known from the patent literature (see U.S. Pat. No. 4,780,127) are excluded.

Preferred substituents or groupings in the formulae mentioned above and below are illustrated below.

Q preferably represents O.

$R^1$ preferably represents hydrogen, represents halogen, represents optionally halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl having 1 to 6 carbon atoms, represents alkylthio having 1 to 6 carbon atoms, or represents phenyl.

$R^2$ preferably represents hydrogen, represents halogen, represents optionally halogen-substituted alkyl having 1 to 6 carbon atoms, or together with $R^1$ represents O (oxygen) or alkanediyl (alkylene) having 2 to 5 carbon atoms.

$R^3$, $R^4$ preferably represent, independently of one another, hydrogen, nitro, cyano, carboxyl, carbamoyl, thiocarbamoyl, halogen, represents in each case optionally halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl; alkoxy, alkylthio, alkylsulphinyl or alkylsulphonyl having in each case up to 4 carbon atoms in the alkyl groups, or represents alkylamino, dialkylamino, dialkylaminocarbonyl or dialkylaminosulphonyl having in each case up to 4 carbon atoms in the alkyl groups.

$R^5$ preferably represents hydrogen, represents in each case optionally cyano-, halogen- or $C_1$-$C_4$-alkoxy-substituted alkyl, alkoxy, alkylthio, alkylsulphinyl, alkylsulphonyl having in each case 1 to 6 carbon atoms in the alkyl groups, represents in each case optionally cyano- or halogen-substituted alkenyl or alkinyl having in each case 3 to 6 carbon atoms in the alkenyl or alkinyl groups, represents in each case optionally cyano-, halogen- or $C_1$-$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally nitro-, cyano-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryl, arylthio, arylsulphinyl, arylsulphonyl or arylalkyl having in each case 6 or 10 carbon atoms in the aryl groups and optionally 1 to 4 carbon atoms in the alkyl moiety, or represents the grouping —C(Q)-Z.

Y preferably represents hydroxyl, halogen, represents in each case optionally cyano-, halogen- or $C_1$-$C_4$-alkoxy-substituted alkoxy, alkylthio, alkylsulphinyl, alkylsulphonyl, alkylcarbonyloxy, alkoxycarbonyloxy, alkylaminocarbonyloxy or alkylsulphonyloxy having in each case 1 to 6 carbon atoms in the alkyl groups, represents in each case optionally cyano- or halogen-substituted alkenyloxy or alkinyloxy having in each case 3 to 6 carbon atoms, or represents in each case optionally nitro-, cyano-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkylsulphinyl-, $C_1$-$C_4$-halogenoalkylsulphinyl-, $C_1$-$C_4$-alkylsulphonyl- or $C_1$-$C_4$-halogenoalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl groups and optionally 1 to 4 carbon atoms in the alkyl moiety.

Z preferably represents hydrogen, amino, cyanoamino, nitroamino, hydroxyamino, hydrazino, $C_1$-$C_4$-alkyl-carbonyl, $C_1$-$C_4$-alkoxy-carbonyl,
represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, having at least two C atoms, alkoxy, alkylthio, alkylamino, alkoxyamino, alkylhydrazino, alkylcarbonylhydrazino, alkoxycarbonylhydrazino or alkylsulphonylhydrazino having in each case 1 to 6 carbon atoms in the alkyl groups,
represents dialkylamino, N-alkyl-alkoxyamino or dialkylhydrazino having in each case 1 to 4 carbon atoms in the alkyl groups, represents in each case optionally halogen-substituted alkenyl, alkenyloxy, alkenylamino, alkenyloxyamino, alkinyl, alkinyloxy or alkinylamino having in each case 2 to 6 carbon atoms,
represents in each case optionally cyano-, halogen- or $C_1$-$C_4$-alkyl substituted cycloalkyl, cycloalkyloxy, cycloalkylamino, cycloalkylhydrazino, cycloalkylalkyl, cycloalkylalkoxy or cycloalkylalkylamino having in each case 3 to 6 carbon atoms in the cycloalkyl group and optionally 1 to 4 carbon atoms in the alkyl moiety,
represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy- or $C_1$-$C_4$-alkoxy-carbonyl-substituted aryl, arylcarbonyl, aryloxy, aryloxycarbonyl, arylthio, arylamino, arylhydrazino, arylalkyl, arylalkoxy, arylalkylthio or arylalkylamino having in each case 6 or 10 carbon atoms in the aryl group and optionally 1 to 4 carbon atoms in the alkyl moiety, or
represents in each case optionally nitro-, cyano-, halogen-, $C_1$-$C_4$-alkyl-, $C_1$-$C_4$-halogenoalkyl-, $C_1$-$C_4$-alkoxy-, $C_1$-$C_4$-halogenoalkoxy-, $C_1$-$C_4$-alkylthio-, $C_1$-$C_4$-halogenoalkylthio- or $C_1$-$C_4$-alkoxy-carbonyl- or $C_3$-$C_6$-cycloalkyl-substituted monocyclic or bicyclic heterocyclyl, heterocyclyloxy, heterocyclylthio, heterocyclylamino, the grouping —N=(heterocyclyl), heterocyclylalkyl, heterocyclylalkoxy, heterocyclylalkylthio or heterocyclylalkylamino, where in each case the heterocyclyl grouping contains up to 10 carbon atoms and additionally at least one heteroatom selected from the group consisting of nitrogen (but at most 5 N atoms), oxygen (but at most 2 O atoms), sulphur (but at most 2 S atoms), SO or $SO_2$ and optionally additionally one group selected from the group consisting of oxo (C=O), thioxo (C=S), imino (C=NH), cyanoimino (C=N—CN) and nitroimino (C=N—$NO_2$) and where, if appropriate, the alkyl moiety contains 1 to 4 carbon atoms.

$R^1$ particularly preferably represents hydrogen, fluorine, chlorine or bromine, represents in each case optionally fluorine-, chlorine-, methoxy-, ethoxy-, n- or i-propoxy-, methylthio-, ethylthio-, n- or i-propylthio, methylsulphinyl-, ethylsulphinyl-, methylsulphonyl- or ethylsulphonyl-substituted methyl, ethyl, n- or i-propyl, n-, i-, s- or t-butyl, methylthio, ethylthio, n- or i-propylthio, n-, i-, s- or t-butylthio, or represents phenyl.

$R^2$ particularly preferably represents hydrogen, fluorine, chlorine or bromine, represents in each case optionally fluorine- or chlorine-substituted methyl, ethyl, n- or i-propyl, n-, i-, s- or t-butyl, or optionally together with $R^1$ also represents O (oxygen), ethane-1,2-diyl, propane-1,3-diyl or butane-1,4-diyl.

$R^3$, $R^4$ particularly preferably represent, independently of one another, hydrogen, nitro, cyano, carboxyl, carbamoyl, thiocarbamoyl, fluorine, chlorine, bromine, iodine, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, dimethylaminocarbonyl, diethylaminocarbonyl, dimethylaminosulphonyl or diethylaminosulphonyl.

$R^5$ particularly preferably represents hydrogen, represents in each case optionally cyano-, fluorine-, chlorine-, bromine-, methoxy-, ethoxy-, n- or i-propoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, methylamino, ethylamino, n- or i-propylamino, n-, i-, s- or t-butylamino, represents dimethylamino or diethylamino, represents in each case optionally fluorine-, chlorine- and/or bromine-substituted ethenyl, propenyl, butenyl, pentenyl, ethinyl, propinyl, butinyl or pentinyl, represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylthio, phenylsulphinyl, phenylsulphonyl, naphthyl, phenylmethyl, phenylethyl, naphthylmethyl or naphthylethyl or represents the grouping —C(Q)-Z.

Y particularly preferably represents hydroxyl, formyloxy, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- and/or bromine-substituted propenyloxy, butenyloxy, propinyloxy or butinyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl.

Z particularly preferably represents hydrogen, amino, cyanoamino, nitroamino, hydroxyamino, hydrazino,
represents cyano-, fluorine-, chlorine-, methoxy-, ethoxy-, n- or i-propoxy-, methylthio-, ethylthio-, n- or i-propylthio-, methylsulphinyl- or, ethylsulphonyl-substituted methyl,
represents in each case optionally cyano-, fluorine-, chlorine-, methoxy-, ethoxy-, n- or i-propoxy-, methylthio-, ethylthio-, n- or i-propylthio-, methylsulphinyl-ethylsulphinyl-, n- or i-propylsulphinyl-, methylsulphonyl- or ethylsulphonyl-substituted ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, methoxyamino, ethoxyamino, n- or i-propoxyamino, n-, i-, s- or t-butoxyamino, methylhydrazino, ethylhydrazino, n- or i-propylhydrazino, n-, i-, s- or t-butylhydrazino, represents dimethylamino, diethylamino, N-methyl-methoxyamino or dimethylhydrazino,
represents in each case optionally fluorine-, chlorine- and/or bromine-substituted ethenyl, propenyl, butenyl, pentenyl, ethinyl, propinyl, butinyl, pentinyl, propenyloxy, butenyloxy, pentenyloxy, propenylthio, butenylthio, pentenylthio, propenylamino, butenylamino, pentenylamino, propenyloxyamino, butenyloxyamino, pentenyloxyamino, ethinyl, propinyl, butinyl, pentinyl, propinyloxy, butinyloxy, pentinyloxy, propinylamino, butinylamino or pentinylamino,
represents in each case optionally cyano-, fluorine-, chlorine-, bromine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylhydrazino, cyclobutylhydrazino, cyclopentylhydrazino, cyclohexylhydrazino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino,
represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, naphthyl, naphthyloxy, naphthylthio, naphthylamino, phenylmethyl, phenylethyl, phenylmethoxy, phenylethoxy, phenylmethylthio, phenylethylthio, phenylmethylamino, phenylethylamino, naphthylmethyl, naphthylethyl, naphthylmethoxy, naphthylethoxy, naphthylmethylamino or naphthylethylamino,
or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, the grouping —N=(heterocyclyl), heterocyclylalkyl, heterocyclylalkoxy or heterocyclylalkylamino from the group consisting of furyl, tetrahydrofuryl, furyloxy, tetrahydrofuryloxy, furylamino, tetrahydrofurylamino, furylmethyl, tetrahydrofurylmethyl, furylmethoxy, tetrahydrofurylmethoxy, furylmethylamino, tetrahydrofurylmethylamino, dioxolanyl, dioxolanylmethyl, dioxolanylmethoxy, dioxolanylmethylamino, thienyl, thienylamino, thienylmethyl, thienylmethylamino, dithiolanyl, dithiolanylmethyl, dithiolanylmethoxy, dithiolanylmethylamino, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diaza-cyclopentyl, oxazolyl, oxazolylamino, dihydrooxazolyl (oxazolinyl), tetrahydrooxazolyl, (oxazolidinyl), isoxazolyl, isoxazolylamino, dihydroisoxazolyl (isoxazolinyl), tetrahydroisoxazolyl (isoxazolidinyl), tetrahydro-(2H)-1,2-oxazin-2-yl, oxazolylmethyl, thiazolyl, thiazolylamino, thiazolylmethyl, dihydrothiazolyl (thiazolinyl), tetrahydrothiazolyl (thiazolidinyl), thiazolinylthio, thiazolinylamino, oxothiazolidinyl, cyanoiminothiazolidinyl, oxadiazolylamino, thiadiazolylamino, triazolylamino, oxotriazolinyl, thioxotriazolinyl, oxotetrazolinyl, oxotetrazolinylmethyl, tetrazolylmethyl, dioxanyl, dioxanylmethyl, dioxanylmethoxy, dioxanylmethylamino, dithianyl, dithianylmethyl, dithianylmethoxy, dithianylmethylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, morpholinylamino, piperazinyl, pyridinyl, pyridinyloxy, pyridinylthio, pyridinylamino, 2-(1H)-pyridineimino, pyridinylmethyl, pyridinylmethoxy, pyrimidinyl, pyrimidinyloxy, pyrimidinylthio, pyrimidinylamino, pyrimidinylmethyl or pyrimidinylmethoxy.

$R^1$ very particularly preferably represents hydrogen, represents in each case optionally fluorine- or chlorine-substituted methyl, ethyl, n- or i-propyl, methylthio, ethylthio, n- or i-propylthio, or represents phenyl.

$R^2$ very particularly preferably represents hydrogen, represents in each case optionally fluorine- or chlorine-substituted methyl, ethyl, n- or i-propyl, or together with $R^1$ optionally also represents ethane-1,2-diyl, propane-1,3-diyl or butane-1,4-diyl.

$R^3$, $R^4$ very particularly preferably represent, independently of one another, hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^5$ very particularly preferably represents hydrogen, represents in each case optionally cyano-, fluorine-, chlorine-, methoxy- or ethoxy-substituted methyl, ethyl, n- or i-propyl, n- or i-butyl, represents methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, methylamino, ethylamino, n- or i-propylamino or dimethylamino, represents in each case optionally fluorine- and/or chlorine-substituted propenyl, butenyl, propinyl or butinyl, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylthio, phenylsulphinyl, phenylsulphonyl, phenylmethyl or phenylethyl, or represents the grouping —C(Q)-Z.

Y very particularly preferably represents hydroxyl, represents in each case optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- and/ or bromine-substituted propenyloxy, butenyloxy, propinyloxy or butinyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl.

Z very particularly preferably represents amino, cyanoamino, hydrazino, represents cyano-, fluorine-, chlorine-, methoxy-ethoxy-, n- or i-propoxy-, methylthio-, ethylthio-, n- or i-propylthio-, methylsulphinyl-, ethylsulphinyl-, n- or i-propylsulphinyl-, methylsulphonyl-, or ethylsulphonyl-substituted methyl, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted ethyl, n- or i-propyl, n-, i-, s- or t-butyl, methoxy, ethoxy, n- or i-propoxy, methylthio, ethylthio, n- or i-propylthio, methylamino, ethylamino, n- or i-propylamino, methoxyamino, ethoxyamino, n- or i-propoxyamino, methylhydrazino, ethylhydrazino, n- or i-propylhydrazino, n-, i-, s- or t-butylhydrazino, represents dimethylamino, N-methylmethoxyamino or dimethylhydrazino, represents in each case optionally fluorine- and/or chlorine-substituted ethenyl, propenyl, butenyl, ethinyl, propinyl, butinyl, propenyloxy, butenyloxy, propenylthio, butenylthio, propenylamino, butenylamino, propenyloxyamino, butenyloxyamino, ethinyl, propinyl, butinyl, propinyloxy, butinyloxy, propinylamino or butinylamino, represents in each case optionally cyano-, fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopentylhydrazino, cyclohexylhydrazino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, phenylmethyl, phenylethyl, phenylmethoxy, phenylethoxy, phenylmethylthio, phenylethylthio, phenylmethylamino or phenylethylamino, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl-, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, the grouping —N=(heterocyclyl), heterocyclylalkyl, heterocyclylalkoxy or heterocyclylalkylamino from the group consisting of furyl, tetrahydrofuryl, furyloxy, tetrahydrofuryloxy, furylamino, tetrahydrofurylamino, furylmethyl, tetrahydrofurylmethyl, furylmethoxy, tetrahydrofurylmethoxy, furylmethylamino, tetrahydrofurylmethylamino, dioxolanyl, dioxolanylmethyl, dioxolanylmethoxy, dioxolanylmethylamino, thienyl, thienylmethyl, dithiolanyl, dithiolanylmethyl, dithiolanylmethoxy, dithiolanylmethylamino, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diaza-cyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydro-(2H)-1,2-oxazin-2-yl, tetrahydroisoxazolyl (isoxazolidinyl), thiazolyl, thiazolylmethyl, dihydrothiazolyl (thiazolinyl), tetrahydrothiazolyl (thiazolidinyl), thiazoleimino, oxothiazolidinyl, cyanoiminothiazolidinyl, oxadiazolylamino, thiadiazolylamino, oxotriazolinyl, oxotetrazolinylmethyl, tetrazolylmethyl, oxotetrazolinyl, oxotetrazolinylmethyl, tetrazolylmethyl, dioxanyl, dioxanylmethyl, dioxanylmethoxy, dioxanylmethylamino, dithianyl, dithianylmethyl, dithianylmethoxy, dithianylmethylamino, triazolylamino, piperidinyl, piperidinylamino, 2-(1H)-pyridineimino, oxopiperidinyl, 2-oxo-1,3-diaza-cyclohexyl, 2-oxo-1-aza-cycloheptyl, 2-oxo-1,3-diaza-cycloheptyl, morpholinyl, morpholinylamino, piperazinyl, pyridinyl, pyridinyloxy, pyridinylamino, pyridinylmethyl, pyridinylmethoxy, pyrimidinyl, pyrimidinyloxy, pyrimidinylmethyl or pyrimidinylmethoxy.

$R^1$ and $R^2$ most preferably represent hydrogen.

$R^3$ most preferably represents hydrogen, fluorine, chlorine, methyl, ethyl, trifluoromethyl, trichloromethyl, methoxy, ethoxy, methylsulphonyl or ethylsulphonyl.

$R^4$ most preferably represents hydrogen, fluorine, chlorine, methyl, ethyl, trifluoromethyl, trichloromethyl, methoxy, ethoxy, methylsulphonyl or ethylsulphonyl.

$R^5$ most preferably represents hydrogen.

Y most preferably represents hydroxyl.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

Here, the abovementioned compounds N-[2,6-dichloro-3-[(3,3-dimethyl-2,6-dioxo-cyclohexyl)-carbonyl]-phenyl]-acetamide, N-[2-chloro-3-[(2,6-dioxo-cyclohexyl)-carbonyl]-4-nitro-phenyl]-acetamide, N-[2-chloro-3-[(2,6-dioxo-cyclohexyl)-carbonyl]-phenyl]-acetamide and N-[2,6-dichloro-3-[(2,6-dioxo-cyclohexyl)-carbonyl]-phenyl]-acetamide (cf. U.S. Pat. No. 4,780,127), which are known from the patent literature, are excluded.

A very particularly preferred group are those compounds of the general formula (I) in which Q represents O or S, $R^1$ represents hydrogen, represents in each case optionally fluorine- or chlorine-substituted methyl, ethyl, n- or i-propyl, methylthio, ethylthio, n- or i-propylthio, or represents phenyl, $R^2$ represents hydrogen, represents in each case optionally fluorine- or chlorine-substituted methyl, ethyl, n- or i-propyl, or together with $R^1$ optionally also represents ethane-1,2-diyl, propane-1,3-diyl or butane-1,4-diyl, $R^3$, $R^4$ represent, independently of one another, hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^5$ represents hydrogen, represents in each case optionally cyano-, fluorine-, chlorine-, methoxy- or ethoxy-substituted methyl, ethyl, n- or i-propyl, n- or i-butyl, represents methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, methylamino, ethylamino, n- or i-propylamino or dimethylamino, represents in each case optionally fluorine- and/or chlorine-substituted propenyl, butenyl, propinyl or butinyl, represents in each case optionally cyano-, fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenylthio, phenylsulphinyl, phenylsulphonyl, phenylmethyl or phenylethyl, or represents the grouping —C(Q)-Z, Y represents hydroxyl, represents in each case optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- and/or bromine-substituted propenyloxy, butenyloxy, propinyloxy or butinyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl, and Z represents amino, cyanoamino, hydrazino, represents cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted ethyl, n- or i-propyl, n-, i-, s- or t-butyl, methoxy, ethoxy, n- or i-propoxy, methylthio, ethylthio, n- or i-propylthio, methylamino, ethylamino, n- or i-propylamino, methoxyamino, ethoxyamino, n- or i-propoxyamino, methylhydrazino, ethylhydrazino, n- or i-propylhydrazino, n-, i-, s- or t-butylhydrazino, represents dimethylamino, N-methylmethoxyamino or dimethylhydrazino, represents in each case optionally fluorine- and/or chlorine-substituted ethenyl, propenyl, butenyl, ethinyl, propinyl, butinyl, propenyloxy, butenyloxy, propenylthio, butenylthio, propenylamino, butenylamino, propenyloxyamino, butenyloxyamino, ethinyl, propinyl, butinyl, propinyloxy, butinyloxy, propinylamino or butinylamino, represents in each case optionally cyano-, fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopentylhydrazino, cyclohexylhydrazino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylamino, cyclobutylmethylamino, cyclopentylmethylamino or cyclohexylmethylamino, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methoxycarbonyl-, ethoxycarbonyl-, n- or i-propoxycarbonyl-substituted phenyl, phenylcarbonyl, phenoxy, phenoxycarbonyl, phenylthio, phenylamino, phenylhydrazino, phenylmethyl, phenylethyl, phenylmethoxy, phenylethoxy, phenylmethylthio, phenylethylthio, phenylmethylamino or phenylethylamino, or represents in each case optionally nitro-, cyano-, fluorine-, chlorine-, bromine-, methyl-, ethyl-, n- or i-propyl-, n-, i-, s- or t-butyl-, difluoromethyl-, trifluoromethyl, dichloromethyl-, trichloromethyl-, chlorodifluoromethyl-, fluorodichloromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methoxycarbonyl-, ethoxycarbonyl-, n- or i-propoxycarbonyl-substituted monocyclic or bicyclic heterocyclyl, heterocyclyloxy, heterocyclylamino, heterocyclylalkyl, heterocyclylalkoxy or heterocyclylalkylamino from the group consisting of furyl, tetrahydrofuryl, furyloxy, tetrahydrofuryloxy, furylamino, tetrahydrofurylamino, furylmethyl, tetrahydrofurylmethyl, furylmethoxy, tetrahydrofurylmethoxy, furylmethylamino, tetrahydrofurylmethylamino, dioxolanyl, dioxolanylmethyl, dioxolanylmethoxy, dioxolanylmethylamino, thienyl, thienylmethyl, dithiolanyl, dithiolanylmethyl, dithiolanylmethoxy, dithiolanylmethylamino, pyrrolidinyl, pyrrolidinylamino, oxopyrrolidinyl, pyrrolyl, indolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diaza-cyclopentyl, oxazolyl, oxazolylmethyl, oxotetrazolinylmethyl, tetrazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), thiazolyl, thiazolylmethyl, dihydrothiazolyl (thiazolinyl), tetrahydrothiazolyl (thiazolidinyl), oxothiazolidinyl, cyanoiminothiazolidinyl, oxotriazolinyl, oxotetrazolinyl, dioxanyl, dioxanylmethyl, dioxanylmethoxy, dioxanylmethylamino, dithianyl, dithianylmethyl, dithianylmethoxy, dithianylmethylamino, piperidinyl, piperidinylamino, oxopiperidinyl, 2-oxo-1,3-diaza-cyclohexyl, 2-oxo-1-aza-cycloheptyl, 2-oxo-1,3-diaza-cycloheptyl, morpholinyl, morpholinylamino, piperazinyl, pyridinyl, pyridinyloxy, pyridinylamino, pyridinylmethyl, pyridinylmethoxy, pyrimidinyl, pyrimidinyloxy, pyrimidinylmethyl or pyrimidinylmethoxy.

Particular emphasis is given to the compounds of the formulae (I-1) to (I-3):

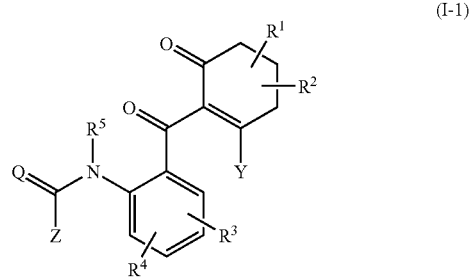

(I-1)

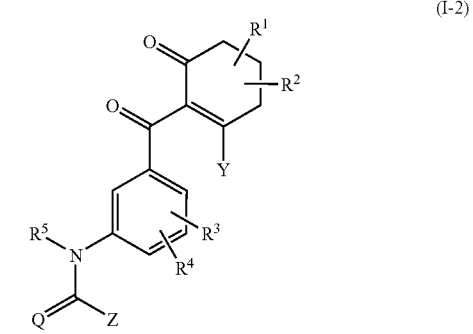

(I-2)

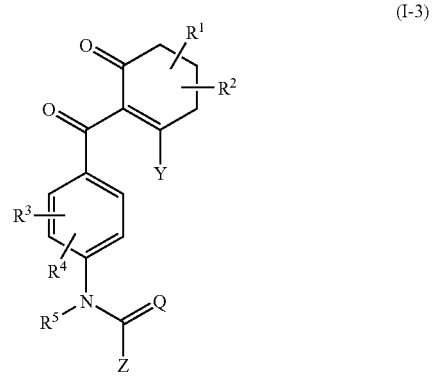

(I-3)

Here, Q, $R^1$, $R^2$, $R^3$, $R^4$, $R^5$, Y and Z each have the meanings listed above as being very particularly preferred.

Again, the radicals $R^3$ and $R^4$ are preferably located on positions (2) and (4), respectively, of the phenyl ring.

The abovementioned general or preferred radical definitions apply both to the end products of the formula (I) and, correspondingly, to the starting materials or the intermediates required in each case for the preparation. These radical definitions can be combined with one another as desired, i.e. including combinations between the given preferred ranges.

Unless specified otherwise, the following definitions apply in the definitions given above and below:

Saturated or unsaturated hydrocarbon chains, such as alkyl, alkanediyl, alkenyl or alkinyl, also in combination with heteroatoms, such as, for example, alkoxyl, alkylthio or alkylamino, are in each case straight-chain or branched. Unless specified otherwise, preference is given to hydrocarbon chains having 1 to 6 carbon atoms.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated, unsaturated or aromatic cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If the ring contains a plurality of oxygen atoms, these are not adjacent. If appropriate, the cyclic compounds form a polycyclic ring system together with further carbocyclic or heterocyclic fused-on or bridged rings. A polycyclic ring system can be attached via the heterocyclic ring or a fused-on carbocyclic ring. Preference is given to mono- or bicyclic ring systems, in particular to monocyclic ring systems having 5 or 6 ring members and bicyclic ring systems having 7 to 9 ring members.

Cycloalkyl represents saturated carbocyclic compounds which may optionally form a polycyclic ring system together with other carbocyclic fused-on or bridged rings.

Unless specified otherwise, preference is given to cyclopropyl, cyclopentyl and cyclohexyl.

The novel substituted benzoylcyclohexenones of the general formula (I) have strong and selective herbicidal activity.

The novel substituted benzoylcyclohexenones of the general formula (I) are obtained when cyclohexanediones ("hydroxycyclohexenones") of the general formula (II)

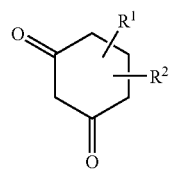

in which $R^1$ and $R^2$ have the meaning given above, are reacted with substituted benzoic acids of the general formula (III)

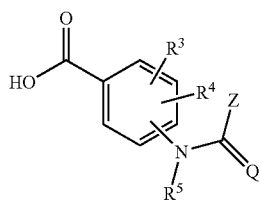

in which

Q, $R^3$, $R^4$, $R^5$ and Z have the meaning given above, or with reactive derivatives thereof, such as, for example, with corresponding acid halides, acid anhydrides, acid cyanides or esters if appropriate in the presence of a dehydrating agent, if appropriate in the presence of one or more reaction auxiliaries and if appropriate in the presence of one or more diluents, and, if appropriate, electrophilic or nucleophilic substitutions and/or oxidations or reductions within the scope of the definition of the substituents are subsequently carried out in a customary manner on the resulting compounds of the formula (I), or the compounds of the formula (I) are converted in a customary manner into salts.

In principle, the novel substituted benzoylcyclohexenones of the general formula (I) can also be obtained as shown schematically below:

Reaction of aminobenzoylcyclohexenones of the general formula (IV) with halogeno(thio)carbonyl compounds of the general formula (V) or, if appropriate, with corresponding iso(thio)cyanates (here, Q, $R^1$, $R^2$, $R^3$, $R^4$, $R^5$, Y and Z have the meanings given above, X represents halogen):

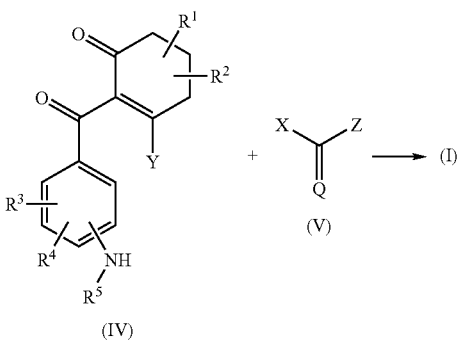

The formulae (IV) and (V) provide general definitions of the compounds to be used as starting materials in the processes (α) and (β) according to the invention. In the formulae (IV) and (V), Q, $R^1$, $R^2$, $R^3$, $R^4$, $R^5$, Y and Z preferably have those meanings which have already been mentioned above, in connection with the description of the compounds of the formula (I) according to the invention, as being preferred, particularly preferred, very particularly preferred or most preferred for Q, $R^1$, $R^2$, $R^3$, $R^4$, $R^5$, Y and Z.

The starting materials of the formula (V) are compounds known to the person skilled in the art.

The starting materials of the formula (IV) can be obtained in a manner known to the person skilled in the art.

Reaction of iso(thio)cyanatobenzoylcyclohexenones of the general formula (VI) with nucleophilic compounds of the general formula (VII); (here, Q, $R^1$, $R^2$, $R^3$, $R^4$, Y and Z have the meanings given above):

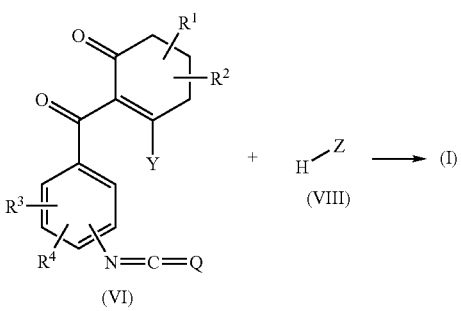

Using, for example, cyclohexane-1,3-dione and 2-chloro-4-[(dimethylaminocarbonyl)-(methylamino)]-benzoic acid as starting materials, the course of the reaction in the process according to the invention can be illustrated by the equation below:

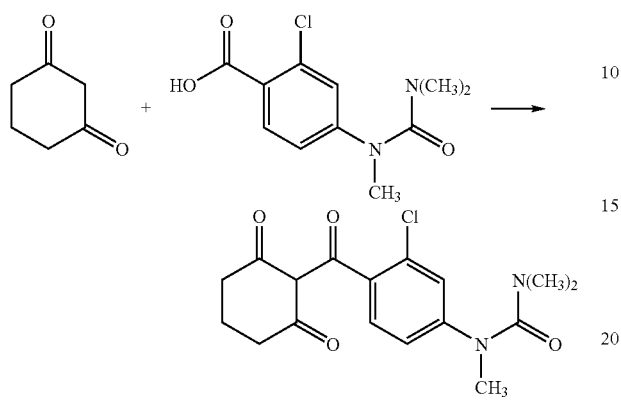

The formula (II) provides a general definition of the cyclohexanediones to be used as starting materials in the process according to the invention for preparing compounds of the general formula (I). In the general formula (II), $R^1$ and $R^2$ preferably have those meanings which have already been mentioned above, in connection with the description of the compounds of the general formula (I) according to the invention, as being preferred, particularly preferred, very particularly preferred or most preferred for $R^1$ and $R^2$.

The starting materials of the general formula (II) are known and/or can be prepared by processes known per se.

The formula (III) provides a general definition of the substituted benzoic acids further to be used as starting materials in the process according to the invention. In the formula (III), Q, $R^3$, $R^4$, $R^5$ and Z preferably have those meanings which have already been mentioned above, in connection with the description of the compounds of the formula (I) according to the invention, as being preferred, particularly preferred, very particularly preferred or most preferred for Q, $R^3$, $R^4$, $R^5$ and Z.

The starting materials of the general formula (III) are known and/or can be prepared by processes known per se (cf. JP-A-11292849, Preparation Examples).

The substituted benzoic acids of the general formula (III) are obtained when benzoic acid esters of the general formula (IIIa)

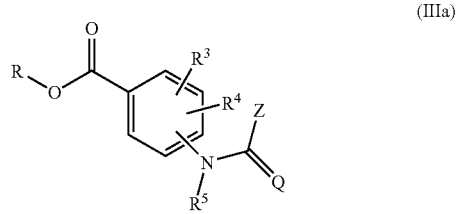

(IIIa)

in which

Q, $R^3$, $R^4$, $R^5$ and Z have the meaning given above and

R represents alkyl, in particular methyl or ethyl, are reacted with water, if appropriate in the presence of a hydrolysis auxiliary, such as, for example, aqueous sodium hydroxide solution, and if appropriate in the presence of a diluent, such as, for example, tetrahydrofuran, at temperatures between 0° C. and 100° C. (cf. the Preparation Examples).

The benzoic acid esters of the general formula (IIIa) required as precursors are known and/or can be prepared by processes known per se (cf. JP-A-11292849, Preparation Examples).

The benzoic acid esters of the general formula (IIIa) are obtained when (α) aminobenzoic acid esters of the general formula (IX)

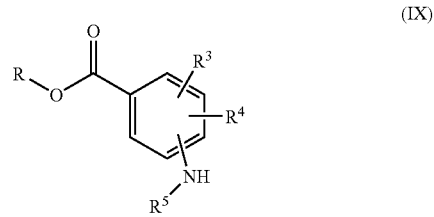

(IX)

in which

Q, $R^3$, $R^4$, $R^5$ and Z have the meaning given above and

R represents alkyl, in particular methyl or ethyl, are reacted with halogeno(thio)carbonyl compounds of the general formula (VI)

(VI)

in which

Q and Z have the meaning given above and

X represents halogen, in particular fluorine, chlorine or bromine, or, if appropriate, with corresponding iso(thio)cyanatesif appropriate in the presence of an acid acceptor, such as, for example, potassium carbonate or triethylamine, and if appropriate in the presence of a diluent, such as, for example, methyl isobutyl ketone or acetonitrile, at temperatures between 0° C. and 100° C. (cf. the Preparation Examples), or when (β) iso(thio)cyanatobenzoic acid esters of the general formula (X)

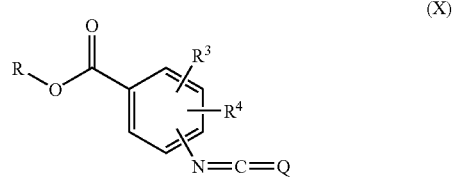

(X)

in which

Q, $R^3$ and $R^4$ have the meaning given above and

R represents alkyl, in particular methyl or ethyl, are reacted with nucleophilic compounds of the general, formula (VIII)

(VIII)

in which

Z has the meaning given above, if appropriate in the presence of a reaction auxiliary, such as, for example, triethylamine, and if appropriate in the presence of a diluent, such as, for example, acetonitrile or toluene, at temperatures between 10° C. and 120° C. (cf. the Preparation Examples).

The formulae (IX), (VI), (X) and (VI) provide general definitions of the compounds to be used as starting materials in the processes (α) and (β) according to the invention. In the formulae (IX), (VI), (X) and (VII), Q, $R^3$, $R^4$, $R^5$ and Z preferably have those meanings which have already been mentioned above, in connection with the description of the compounds of the formula (I) according to the invention, as being preferred, particularly preferred, very particularly preferred or most preferred for Q, $R^3$, $R^4$, $R^5$ and Z.

The starting materials of the formulae (VI) and (VIII) are compounds known to the person skilled in the art.

The starting materials of the formulae (IX) and (X) can be obtained in a manner known to the person skilled in the art.

The process according to the invention for preparing the novel substituted benzoylcyclohexenones of the general formula (I) is preferably carried out using a dehydrating agent. Here, suitable dehydrating agents are the chemicals customarily suitable for binding water.

Examples which may be mentioned are dicyclohexylcarbodiimide, propanephosphonic anhydride and carbonyl-bis-imidazole.

Dehydrating agents which may be mentioned as being particularly suitable are dicyclohexylcarbodiimide and propanephosphonic anhydride.

The process according to the invention for preparing the novel substituted benzoylcyclohexenones of the general formula (I) is, if appropriate, carried out using a reaction auxiliary.

Examples of reaction auxiliaries which may be mentioned are sodium cyanide, potassium cyanide, acetone cyanohydrin, 2-cyano-2-(trimethylsilyloxy)-propane and trimethylsilyl cyanide.

Trimethylsilyl cyanide may be mentioned as being a particularly suitable reaction auxiliary.

The process according to the invention is preferably carried out using one or more reaction auxiliaries. Reaction auxiliaries suitable for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, N-ethyl-piperidine, N-methyl-morpholine, N-ethyl-morpholine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Further reaction auxiliaries suitable for the process according to the invention are phase-transfer catalysts. Examples of such catalysts which may be mentioned are:

tetrabutylammonium bromide, tetrabutylammonium chloride, tetraoctylammonium chloride, tetrabutylammonium hydrogensulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

The process according to the invention for preparing the compounds of the general formula (I) is preferably in each case carried out using one or more diluents. Diluents suitable for carrying out the process according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxale, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether.

When carrying out the process according to the invention, the reaction temperatures can be varied within a relatively wide range. In general, the process is carried out at temperatures between 10° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used. The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thiaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop(-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides; bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agrochemical active compounds—, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defense of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defense of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula I or the active compound mixtures according to the invention where in addition to the good control of weed plants, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The following examples show the preparation and use of the active compounds according to the invention:

PREPARATION EXAMPLES

Example 1-1

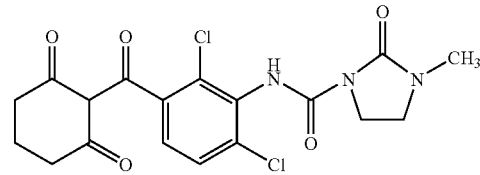

A mixture of 2.80 g (8.43 mmol) of 2,4-dichloro-3-[[(3-methyl-2-oxo-1-imidazolidinyl)-carbonyl]-amino]-benzoic acid, 0.945 g (8.43 mmol) of cyclohexane-1,3-dione, 2.10 g (10.1 mmol) of dicyclohexylcarbodiimide and 30 ml of acetonitrile is stirred at room temperature (about 20° C.) for 18 hours and then filtered. The filtrate is treated with 0.335 g (3.37 mmol) of trimethylsilyl cyanide and 1.70 g (16.9 mmol) of triethylamine and the mixture is stirred at room temperature for 18 hours and then concentrated under reduced pressure. The residue is stirred with 10% strength aqueous sodium carbonate solution and then extracted with diethyl ether. The organic phase is separated off (and discarded) and the aqueous solution is then acidified with conc. hydrochloric acid and the resulting crystalline product is isolated by filtration with suction.

This gives 2.20 g (49% of theory) of N-[2,6-dichloro-3-[(2,6-dioxo-cyclohexyl)-carbonyl]-phenyl]-3-methyl-2-oxo-1-imidazolidinecarboxamide.

log P (pH=2.3): 2.07.

Analogously to Example 1 and in accordance with the general description of the preparation process according to the invention it is also possible to prepare, for example, the compounds of the general formula (I)—or those of the formulae (I-1), (I-2) or (I-3)—listed in Tables I-1 to I-5 below.

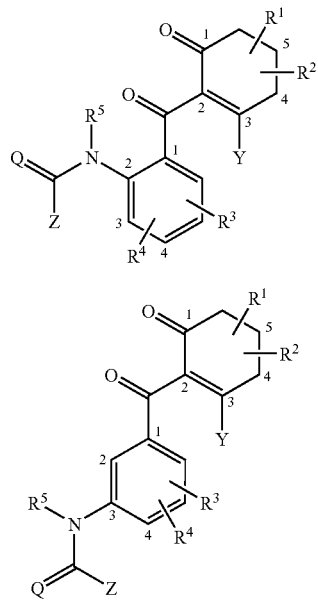

(I-1)

(I-2)

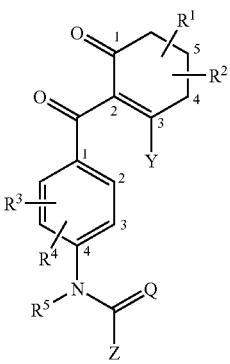

(I-3)

TABLE 1-1

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-2 | O | (2) Cl | (4) Cl | H | 1-methyl-3-ethyl-imidazolidin-2-one | (I-2) logP = 2.33[a] |
| 1-3 | O | (2) Cl | (4) Cl | H | N(OCH₃)(CH₃) | (I-2) logP = 1.97[a] |
| 1-4 | O | (2) Cl | (4) Cl | H | 1,3-dimethyl-tetrahydropyrimidin-2-one | (I-2) logP = 2.33[a] |
| 1-5 | O | (2) Cl | (4) Cl | H | N-methylmorpholine | (I-2) logP = 1.60[a] |
| 1-6 | O | (2) Cl | (4) Cl | H | NHN(CH₃)₂ methylated | (I-2) logP = 1.81[a] |
| 1-7 | O | (2) Cl | (4) Cl | H | N(C₂H₅)₂ | (I-2) logP = 2.21[a] |
| 1-8 | O | (2) Cl | (4) Cl | H | NHCH₃ | (I-2) logP = 1.46[a] |
| 1-9 | O | (2) Cl | (4) Cl | H | NHC₂H₅ | (I-2) logP = 1.70[a] |
| 1-10 | O | (2) Cl | (4) Cl | H | N(CH₃)₂ | (I-2) logP = 1.64[a] |
| 1-11 | O | (2) Cl | (4) Cl | H | 1,4-dimethylpiperazine | (I-2) |

TABLE 1-1-continued
Examples of compounds of the formula (I)
Here, R¹ and R² each represent hydrogen and Y represents hydroxyl.
| Ex. No. | Q | (position) R³ | (position) R⁴ | R⁵ | Z | Formula physical data |
|---|---|---|---|---|---|---|
| 1-12 | O | (2) Cl | (4) Cl | H | NHC₃H₇-i | (I-2) logP = 1.99[a] |
| 1-13 | O | (2) Cl | (4) Cl | H | 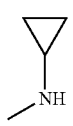 | (I-2) logP = 1.77[a] |
| 1-14 | O | (2) Cl | (4) Cl | H | 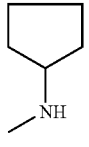 | (I-2) |
| 1-15 | O | (2) Cl | (4) Cl | H | 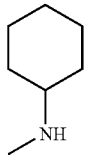 | (I-2) |
| 1-16 | O | (2) Cl | (4) Cl | H | 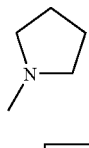 | (I-2) logP = 1.90[a] |
| 1-17 | O | (2) Cl | (4) Cl | H | 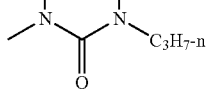 | (I-2) |
| 1-18 | O | (2) Cl | (4) Cl | H | 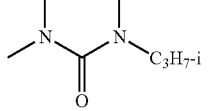 | (I-2) |
| 1-19 | O | (2) Cl | (4) Cl | H | 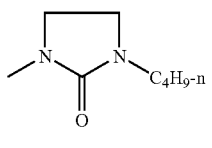 | (I-2) |
| 1-20 | O | (2) Cl | (4) Cl | H | 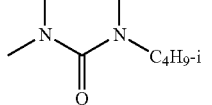 | (I-2) |
| 1-21 | O | (2) Cl | (4) Cl | H | 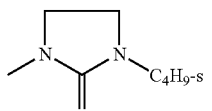 | (I-2) |
| 1-22 | O | (2) Cl | (4) Cl | H | 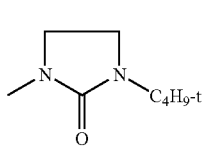 | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-23 | O | (2) Cl | (4) Cl | H | tetrahydropyrimidin-2(1H)-one, N-methyl, N'-C$_2$H$_5$ | (I-2) logP = 2.65[a] |
| 1-24 | O | (2) Cl | (4) Cl | H | tetrahydropyrimidin-2(1H)-one, N-methyl, N'-C$_3$H$_7$-n | (I-2) |
| 1-25 | O | (2) Cl | (4) Cl | H | tetrahydropyrimidin-2(1H)-one, N-methyl, N'-C$_3$H$_7$-i | (I-2) logP = 2.98[a] |
| 1-26 | O | (2) Cl | (4) Cl | H | tetrahydropyrimidin-2(1H)-one, N-methyl, N'-C$_4$H$_9$-n | (I-2) |
| 1-27 | O | (2) Cl | (4) Cl | H | tetrahydropyrimidin-2(1H)-one, N-methyl, N'-C$_4$H$_9$-i | (I-2) |
| 1-28 | O | (2) Cl | (4) Cl | H | tetrahydropyrimidin-2(1H)-one, N-methyl, N'-C$_4$H$_9$-s | (I-2) |
| 1-29 | O | (2) Cl | (4) Cl | H | tetrahydropyrimidin-2(1H)-one, N-methyl, N'-C$_4$H$_9$-t | (I-2) |
| 1-30 | O | (2) Cl | (4) Cl | H | thiazolidin-2-ylidene cyanamide, N-methyl | (I-2) |
| 1-31 | O | (2) Cl | (4) Cl | H | 1,3-dihydro-imidazol-2-one, N-methyl, N'-CH$_3$ | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-32 | O | (2) Cl | (4) Cl | H | 1,3-dioxolan-2-ylmethyl-NH- | (I-2) |
| 1-33 | O | (2) Cl | (4) Cl | H | (tetrahydrofuran-2-yl)methyl-NH- | (I-2) logP = 1.81[a] |
| 1-34 | O | (2) Cl | (4) Cl | H | (tetrahydrofuran-3-yl)methyl-NH- | (I-2) |
| 1-35 | O | (2) Cl | (4) Cl | H | (CH$_3$O)$_2$CH-CH$_2$-NH- | (I-2) logP = 1.72[a] |
| 1-36 | O | (2) Cl | (4) Cl | H | 4,5-dihydrothiazol-2-yl-NH- | (I-2) |
| 1-37 | O | (2) Cl | (4) Cl | H | thiazol-2-yl-NH- | (I-2) |
| 1-38 | O | (2) Cl | (4) Cl | H | 1,3,4-thiadiazol-2-yl-NH- | (I-2) |
| 1-39 | O | (2) Cl | (4) Cl | H | 5-methyl-1,3,4-thiadiazol-2-yl-NH- | (I-2) |

TABLE 1-1-continued

Examples of compounds of the formula (I)
Here, R¹ and R² each represent hydrogen and Y represents hydroxyl.

| Ex. No. | Q | (position) R³ | (position) R⁴ | R⁵ | Z | Formula physical data |
|---|---|---|---|---|---|---|
| 1-40 | O | (2) Cl | (4) Cl | H | $F_3C$-[1,3,4-thiadiazol-2-yl]-NH- | (I-2) logP = 2.78[a] |
| 1-41 | O | (2) Cl | (4) Cl | H | [1,3,4-oxadiazol-2-yl]-NH- | (I-2) |
| 1-42 | O | (2) Cl | (4) Cl | H | [isoxazol-3-yl]-NH- | (I-2) |
| 1-43 | O | (2) Cl | (4) Cl | H | [4,5-dihydrothiazol-2-yl]-S- | (I-2) |
| 1-44 | O | (2) Cl | (4) Cl | H | $SCH_3$ | (I-2) |
| 1-45 | O | (2) Cl | (4) Cl | H | $SC_2H_5$ | (I-2) |
| 1-46 | O | (2) Cl | (4) Cl | H | $SC_3H_7$-n | (I-2) |
| 1-47 | O | (2) Cl | (4) Cl | H | $SC_3H_7$-i | (I-2) |
| 1-48 | O | (2) Cl | (4) Cl | H | $SC_4H_9$-n | (I-2) |
| 1-49 | O | (2) Cl | (4) Cl | H | $CH_2=CH-CH_2-S-$ | (I-2) |
| 1-50 | O | (2) Cl | (4) Cl | H | $CH\equiv C-CH_2-S-$ | (I-2) |
| 1-51 | O | (2) Cl | (4) $SO_2CH_3$ | H | 1-methyl-3-ethyl-imidazolidin-2-on-yl | (I-2) |
| 1-52 | O | (2) Cl | (4) $SO_2CH_3$ | H | $CH_3-N(OCH_3)-CH_3$ wait: N(CH_3)(OCH_3) | (I-2) |
| 1-53 | O | (2) Cl | (4) $SO_2CH_3$ | H | 1,3-dimethyl-tetrahydropyrimidin-2-on-yl | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-54 | O | (2) Cl | (4) SO$_2$CH$_3$ | H | 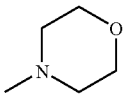 | (I-2) |
| 1-55 | O | (2) Cl | (4) SO$_2$CH$_3$ | H | 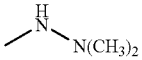 | (I-2) |
| 1-56 | O | (2) Cl | (4) SO$_2$CH$_3$ | H | N(C$_2$H$_5$)$_2$ | (I-2) |
| 1-57 | O | (2) Cl | (4) SO$_2$CH$_3$ | H | NHCH$_3$ | (I-2) |
| 1-58 | O | (2) Cl | (4) SO$_2$CH$_3$ | H | NHC$_2$H$_5$ | (I-2) |
| 1-59 | O | (2) Cl | (4) SO$_2$CH$_3$ | H | N(CH$_3$)$_2$ | (I-2) |
| 1-60 | O | (2) Cl | (4) SO$_2$CH$_3$ | H | 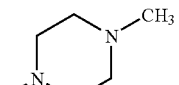 | (I-2) |
| 1-61 | O | (2) Cl | (4) SO$_2$CH$_3$ | H | NHC$_3$H$_7$-i | (I-2) |
| 1-62 | O | (2) Cl | (4) SO$_2$CH$_3$ | H | 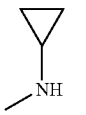 | (I-2) |
| 1-63 | O | (2) Cl | (4) SO$_2$CH$_3$ | H | 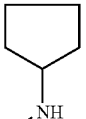 | (I-2) |
| 1-64 | O | (2) Cl | (4) SO$_2$CH$_3$ | H | 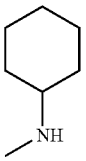 | (I-2) |
| 1-65 | O | (2) Cl | (4) SO$_2$CH$_3$ | H | 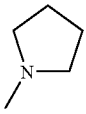 | (I-2) |
| 1-66 | O | (2) Cl | (4) SO$_2$CH$_3$ | H | 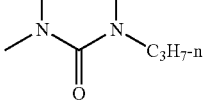 | (I-2) |
| 1-67 | O | (2) Cl | (4) SO$_2$CH$_3$ | H | 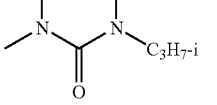 | (I-2) |
| 1-68 | O | (2) Cl | (4) SO$_2$CH$_3$ | H | 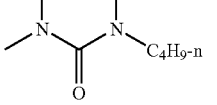 | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-69 | O | (2) Cl | (4) $SO_2CH_3$ | H | imidazolidin-2-one, N-CH$_3$, N-$C_4H_9$-i | (I-2) |
| 1-70 | O | (2) Cl | (4) $SO_2CH_3$ | H | imidazolidin-2-one, N-CH$_3$, N-$C_4H_9$-s | (I-2) |
| 1-71 | O | (2) Cl | (4) $SO_2CH_3$ | H | imidazolidin-2-one, N-CH$_3$, N-$C_4H_9$-t | (I-2) |
| 1-72 | O | (2) Cl | (4) $SO_2CH_3$ | H | tetrahydropyrimidin-2-one, N-CH$_3$, N-$C_2H_5$ | (I-2) |
| 1-73 | O | (2) Cl | (4) $SO_2CH_3$ | H | tetrahydropyrimidin-2-one, N-CH$_3$, N-$C_3H_7$-n | (I-2) |
| 1-74 | O | (2) Cl | (4) $SO_2CH_3$ | H | tetrahydropyrimidin-2-one, N-CH$_3$, N-$C_3H_7$-i | (I-2) |
| 1-75 | O | (2) Cl | (4) $SO_2CH_3$ | H | tetrahydropyrimidin-2-one, N-CH$_3$, N-$C_4H_9$-n | (I-2) |
| 1-76 | O | (2) Cl | (4) $SO_2CH_3$ | H | tetrahydropyrimidin-2-one, N-CH$_3$, N-$C_4H_9$-i | (I-2) |
| 1-77 | O | (2) Cl | (4) $SO_2CH_3$ | H | tetrahydropyrimidin-2-one, N-CH$_3$, N-$C_4H_9$-s | (I-2) |

TABLE 1-1-continued

Examples of compounds of the formula (I)
Here, R¹ and R² each represent hydrogen and Y represents hydroxyl.

| Ex. No. | Q | (position) R³ | (position) R⁴ | R⁵ | Z | Formula physical data |
|---|---|---|---|---|---|---|
| 1-78 | O | (2) Cl | (4) SO$_2$CH$_3$ | H | 1,3-disubstituted tetrahydropyrimidin-2-one (N-CH$_3$, N-C$_4$H$_9$-t) | (I-2) |
| 1-79 | O | (2) Cl | (4) SO$_2$CH$_3$ | H | 3-methyl-2-(cyanoimino)thiazolidine | (I-2) |
| 1-80 | O | (2) Cl | (4) SO$_2$CH$_3$ | H | 1,3-dimethyl-2,3-dihydro-1H-imidazol-2-one | (I-2) |
| 1-81 | O | (2) Cl | (4) SO$_2$CH$_3$ | H | (1,3-dioxolan-2-yl)methyl-NH- | (I-2) |
| 1-82 | O | (2) Cl | (4) SO$_2$CH$_3$ | H | (tetrahydrofuran-2-yl)methyl-NH- | (I-2) |
| 1-83 | O | (2) Cl | (4) SO$_2$CH$_3$ | H | (tetrahydrofuran-3-yl)methyl-NH- | (I-2) |
| 1-84 | O | (2) Cl | (4) SO$_2$CH$_3$ | H | (2,2-dimethoxyethyl)-NH- [CH(OCH$_3$)$_2$-CH$_2$-NH-] | (I-2) |
| 1-85 | O | (2) Cl | (4) SO$_2$CH$_3$ | H | (4,5-dihydrothiazol-2-yl)-NH- | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-86 | O | (2) Cl | (4) SO$_2$CH$_3$ | H | 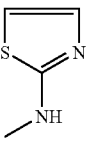 | (I-2) |
| 1-87 | O | (2) Cl | (4) SO$_2$CH$_3$ | H | 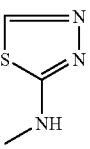 | (I-2) |
| 1-88 | O | (2) Cl | (4) SO$_2$CH$_3$ | H | 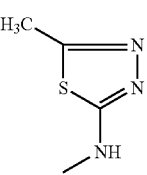 | (I-2) |
| 1-89 | O | (2) Cl | (4) SO$_2$CH$_3$ | H | 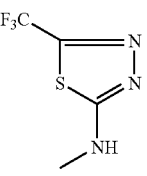 | (I-2) |
| 1-90 | O | (2) Cl | (4) SO$_2$CH$_3$ | H | 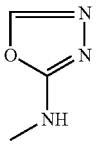 | (I-2) |
| 1-91 | O | (2) Cl | (4) SO$_2$CH$_3$ | H | 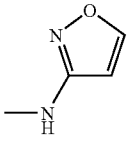 | (I-2) |
| 1-92 | O | (2) Cl | (4) SO$_2$CH$_3$ | H | 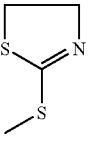 | (I-2) |
| 1-93 | O | (2) Cl | (4) SO$_2$CH$_3$ | H | SCH$_3$ | (I-2) |
| 1-94 | O | (2) Cl | (4) SO$_2$CH$_3$ | H | SC$_2$H$_5$ | (I-2) |
| 1-95 | O | (2) Cl | (4) SO$_2$CH$_3$ | H | SC$_3$H$_7$-n | (I-2) |
| 1-96 | O | (2) Cl | (4) SO$_2$CH$_3$ | H | SC$_3$H$_7$-i | (I-2) |
| 1-97 | O | (2) Cl | (4) SO$_2$CH$_3$ | H | SC$_4$H$_9$-n | (I-2) |
| 1-98 | O | (2) Cl | (4) SO$_2$CH$_3$ | H | 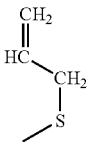 | (I-2) |

TABLE 1-1-continued

Examples of compounds of the formula (I)
Here, R¹ and R² each represent hydrogen and Y represents hydroxyl.

| Ex. No. | Q | (position) R³ | (position) R⁴ | R⁵ | Z | Formula physical data |
|---|---|---|---|---|---|---|
| 1-99 | O | (2) Cl | (4) SO₂CH₃ | H | CH≡C-CH₂-S-CH₂- (allyl propargyl sulfide group) | (I-2) |
| 1-100 | O | (4) CF₃ | — | H | 1,3-dimethyl-imidazolidin-2-one-yl | (I-1) logP = 2.57[a] |
| 1-101 | O | (2) Cl | (4) Cl | H | pyrrolidin-1-yl-amino-methyl | (I-2) logP = 1.94[a] |
| 1-102 | O | (2) Cl | (4) Cl | H | morpholin-4-yl-amino-methyl | (I-2) |
| 1-103 | O | (2) Cl | (4) Cl | H | 1-methyl-3-cyclohexyl-tetrahydropyrimidin-2-one-yl | (I-2) logP = 3.86[a] |
| 1-104 | O | (4) CF₃ | — | CH₃ | 1,3-dimethyl-imidazolidin-2-one-yl | (I-1) logP = 2.04[a] |
| 1-105 | O | (2) Cl | (4) Cl | H | piperidin-1-yl-methyl | (I-2) logP = 2.26[a] |
| 1-106 | O | (2) Cl | (4) Cl | H | NH₂ | (I-2) logP = 1.29[a] |
| 1-107 | O | (2) Cl | (4) Cl | H | NHC₃H₇-n | (I-2) logP = 1.98[a] |
| 1-108 | O | (2) Cl | (4) Cl | H | NH-OCH₃ | (I-2) logP = 1.58[a] |
| 1-109 | O | (2) Cl | (4) Cl | H | N(C₃H₇-n)₂ | (I-2) logP = 2.95[a] |
| 1-110 | O | (2) OCH₃ | — | H | 1,3-dimethyl-imidazolidin-2-one-yl | (I-3) logP = 1.93[a] |
| 1-111 | O | (2) Cl | (4) Cl | H | thiophen-2-yl-methyl | (I-2) logP = 2.34[a] |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-112 | O | (2) Cl | (4) Cl | H | 3-methyl-5-methyl-isoxazole | (I-2) logP = 2.36[a] |
| 1-113 | O | (2) Cl | (4) Cl | H | $C_2H_5$ | (I-2) |
| 1-114 | O | (2) Cl | (4) Cl | H | $CH_2OCH_3$ | (I-2) |
| 1-115 | O | (2) Cl | (4) Cl | H | $C_3H_7\text{-}n$ | (I-2) |
| 1-116 | O | (2) Cl | (4) Cl | H | $C_3H_7\text{-}i$ | (I-2) |
| 1-117 | O | (2) Cl | (4) Cl | H | $C_4H_9\text{-}n$ | (I-2) |
| 1-118 | O | (2) Cl | (4) Cl | H | $C_4H_9\text{-}i$ | (I-2) |
| 1-119 | O | (2) Cl | (4) Cl | H | $C_4H_9\text{-}s$ | (I-2) |
| 1-120 | O | (2) Cl | (4) Cl | H | $C_4H_9\text{-}t$ | (I-2) |
| 1-121 | O | (2) Cl | (4) Cl | H | $CH_2Cl$ | (I-2) |
| 1-122 | O | (2) Cl | (4) Cl | H | $CHCl_2$ | (I-2) |
| 1-123 | O | (2) Cl | (4) Cl | H | $CCl_3$ | (I-2) |
| 1-124 | O | (2) Cl | (4) Cl | H | $CF_3$ | (I-2) |
| 1-125 | O | (2) Cl | (4) Cl | H | cyclopropyl | (I-2) |
| 1-126 | O | (2) Cl | (4) Cl | H | cyclopentyl | (I-2) |
| 1-127 | O | (2) Cl | (4) Cl | H | cyclohexyl | (I-2) |
| 1-128 | O | (2) Cl | (4) Cl | H | phenyl | (I-2) |
| 1-129 | O | (2) Cl | (4) Cl | H | benzyl | (I-2) |
| 1-130 | O | (2) Cl | (4) Cl | H | $CH_3OCH_2CH_2NHCH_2$ | (I-2) |
| 1-131 | O | (2) Cl | (4) Cl | $CH_3$ | $CH_3OCH_2CH_2NHCH_2$ | (I-2) |
| 1-132 | O | (2) Cl | (4) Cl | H | $CH_3OCH_2CH_2N(CH_3)CH_2$ | (I-2) logP = 2.04[a] |

TABLE 1-1-continued
Examples of compounds of the formula (I)
Here, $R^1$ and $R^2$ each represent hydrogen and Y represents hydroxyl.
| Ex. No. | Q | (position) $R^3$ | (position) $R^4$ | $R^5$ | Z | Formula physical data |
|---|---|---|---|---|---|---|
| 1-133 | O | (2) Cl | (4) Cl | CH$_3$ | 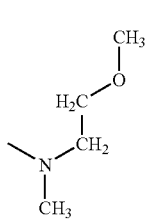 | (I-2) |
| 1-134 | O | (2) Cl | (4) Cl | H | 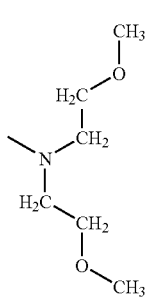 | (I-2) logP = 2.40[a)] |
| 1-135 | O | (2) Cl | (4) Cl | H | 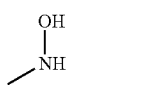 | (I-2) |
| 1-136 | O | (2) Cl | (4) Cl | H | 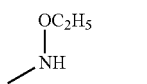 | (I-2) logP = 1.88[a)] |
| 1-137 | O | (2) Cl | (4) Cl | H | 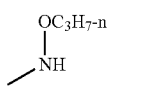 | (I-2) |
| 1-138 | O | (2) Cl | (4) Cl | H | 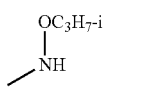 | (I-2) |
| 1-139 | O | (2) Cl | (4) Cl | H | 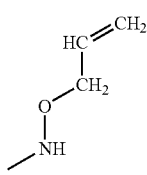 | (I-2) |
| 1-140 | O | (2) Cl | (4) Cl | H | 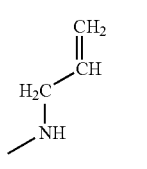 | (I-2) |
| 1-141 | O | (2) Cl | (4) Cl | H | 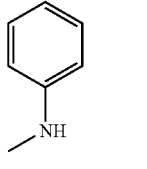 | (I-2) |

TABLE 1-1-continued
Examples of compounds of the formula (I)
Here, R¹ and R² each represent hydrogen and Y represents hydroxyl.
| Ex. No. | Q | (position) R³ | (position) R⁴ | R⁵ | Z | Formula physical data |
|---|---|---|---|---|---|---|
| 1-142 | O | (2) Cl | (4) Cl | H | 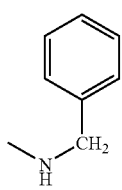 | (I-2) logP = 2.37[a] |
| 1-143 | O | (2) Cl | (4) Cl | H | 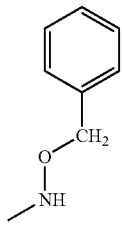 | (I-2) |
| 1-144 | O | (2) Cl | (4) Cl | H | 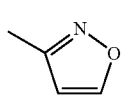 | (I-2) |
| 1-145 | O | (2) Cl | (4) Cl | H | 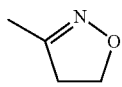 | (I-2) logP = 2.02[a] |
| 1-146 | O | (2) Cl | (4) Cl | H | 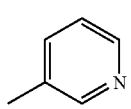 | (I-2) |
| 1-147 | O | (2) Cl | (4) Cl | H | 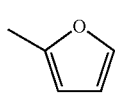 | (I-2) logP = 2.08[a] |
| 1-148 | O | (2) Cl | (4) Cl | H | 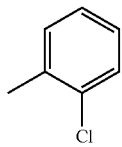 | (I-2) |
| 1-149 | O | (2) Cl | (4) Cl | H | 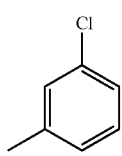 | (I-2) |
| 1-150 | O | (2) Cl | (4) Cl | H | 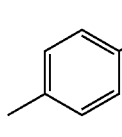 | (I-2) logP = 2.96[a] |
| 1-151 | O | (2) Cl | (4) Cl | H | 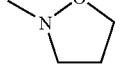 | (I-2) logP = 1.93[a] |
| 1-152 | O | (2) Cl | (4) SO₂CH₃ | H | 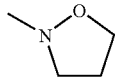 | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-153 | O | (4) $CF_3$ | — | H | isoxazolidin-2-yl (N-CH₂-CH₂-CH₂-O ring) | (I-1) |
| 1-154 | O | (2) $OCH_3$ | — | H | isoxazolidin-2-yl | (I-3) |
| 1-155 | O | (2) $NO_2$ | — | H | isoxazolidin-2-yl | (I-3) |
| 1-156 | O | (4) $CF_3$ | — | H | $N(OCH_3)(CH_3)$ | (I-1) |
| 1-157 | O | (2) $OCH_3$ | — | H | $N(OCH_3)(CH_3)$ | (I-3) |
| 1-158 | O | (2) $NO_2$ | — | H | $N(OCH_3)(CH_3)$ | (I-3) |
| 1-159 | S | (2) Cl | (4) Cl | H | $N(OCH_3)(CH_3)$ | (I-2) logP = 2.28[a] |
| 1-160 | O | (2) Cl | (4) Cl | H | piperidin-1-yl-NH– | (I-2) logP = 2.52[a] |
| 1-161 | O | (2) Cl | (4) Cl | H | $N(OCH_3)(CH_3)$ | (I-2) Y = $SC_6H_5$ logP = 2.98[a] |
| 1-162 | O | (2) Cl | (4) Cl | H | 3-methyl-thiazol-2(3H)-ylidene-amino | (I-2) logP = 1.96[a] |
| 1-163 | O | (2) Cl | (4) Cl | H | 3-ethyl-thiazol-2(3H)-ylidene-amino | (I-2) logP = 2.22[a] |
| 1-164 | O | (2) Cl | (4) Cl | H | 1,2-oxazinan-2-yl (6-membered N-O ring) | (I-2) logP = 2.17[a] |
| 1-165 | O | (2) Cl | (4) Cl | H | $N(C_3H_7\text{-}n)(C_2H_5)$ | (I-2) logP = 2.56[a] |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-166 | O | (2) Cl | (4) Cl | H | $N(CH_3)C_3H_7\text{-}i$ | (I-2) logP = 2.17[a] |
| 1-167 | O | (2) Cl | (4) Cl | H | $\text{N}(OC_2H_5)(CH_3)$ | (I-2) logP = 2.30[a] |
| 1-168 | O | (2) Cl | (4) Cl | H | $NHC_4H_9\text{-}t$ | (I-2) logP = 2.41[a] |
| 1-169 | O | (2) Cl | (4) Cl | H | $\text{N}(C_3H_7\text{-}i)(C_2H_5)$ | (I-2) logP = 2.49[a] |
| 1-170 | O | (2) Cl | (4) Cl | H | $N(CH_3)C_2H_5$ | (I-2) logP = 1.91[a] |
| 1-171 | O | (2) Cl | (4) Cl | H | —NH—CH$_2$—cyclopropyl | (I-2) logP = 2.05[a] |
| 1-172 | O | (2) Cl | (4) Cl | H | —NH—CH$_2$—CH$_2$—CH(OCH$_3$)—CH$_2$ | (I-2) logP = 1.72[a] |
| 1-173 | O | (2) Cl | (4) Cl | H | $\text{N}(C_3H_7\text{-}n)(CH_3)$ | (I-2) logP = 2.22[a] |
| 1-174 | O | (2) Cl | (4) Cl | H | $\text{N}(OC_3H_7\text{-}n)(CH_3)$ | (I-2) |
| 1-175 | O | (2) Cl | (4) Cl | H | $\text{N}(OCH_3)(C_2H_5)$ | (I-2) |
| 1-176 | O | (2) Cl | (4) $SO_2CH_3$ | H | $\text{N}(OCH_3)(C_2H_5)$ | (I-2) |
| 1-177 | O | (2) Cl | (4) Cl | H | $\text{N}(OC_3H_7\text{-}n)(CH_3)$ | (I-2) |
| 1-178 | O | (2) Cl | (4) $SO_2CH_3$ | H | $\text{N}(OC_2H_5)(CH_3)$ | (I-2) |
| 1-179 | O | (2) Cl | (4) Cl | H | $\text{N}(OC_2H_5)(C_2H_5)$ | (I-2) |
| 1-180 | O | (2) Cl | (4) $SO_2CH_3$ | H | $\text{N}(OC_2H_5)(C_2H_5)$ | (I-2) |

TABLE 1-1-continued

Examples of compounds of the formula (I)
Here, R¹ and R² each represent hydrogen and Y represents hydroxyl.

| Ex. No. | Q | (position) R³ | (position) R⁴ | R⁵ | Z | Formula physical data |
|---|---|---|---|---|---|---|
| 1-181 | O | (2) Cl | (4) SO₂CH₃ | H | N-methyl-1,2-oxazinane | (I-2) |
| 1-182 | O | (2) Cl | (4) Cl | H | 2-methylfuran | (I-2) |
| 1-183 | O | (2) Cl | (4) SO₂CH₃ | H | 2-methylfuran | (I-2) |
| 1-184 | O | (2) Cl | (4) SO₂CH₃ | H | 3-methyl-4,5-dihydroisoxazole | (I-2) |
| 1-185 | O | (2) Cl | (4) SO₂CH₃ | H | N-methylpiperidine | (I-2) |
| 1-186 | O | (2) Cl | (4) SO₂CH₃ | H | N-methylaniline | (I-2) |
| 1-187 | O | (2) Cl | (4) Cl | H | N,N-dimethylaniline | (I-2) |
| 1-188 | O | (2) Cl | (4) SO₂CH₃ | H | N,N-dimethylaniline | (I-2) |
| 1-189 | O | (2) Cl | (4) Cl | H | 4-chloro-N-methylaniline | (I-2) |
| 1-190 | O | (2) Cl | (4) SO₂CH₃ | H | 4-chloro-N-methylaniline | (I-2) |

TABLE 1-1-continued
Examples of compounds of the formula (I)
Here, $R^1$ and $R^2$ each represent hydrogen and Y represents hydroxyl.
| Ex. No. | Q | (position) $R^3$ | (position) $R^4$ | $R^5$ | Z | Formula physical data |
|---|---|---|---|---|---|---|
| 1-191 | O | (2) Cl | (4) Cl | H | 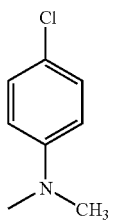 | (I-2) |
| 1-192 | O | (2) Cl | (4) SO$_2$CH$_3$ | H | 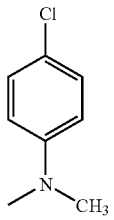 | (I-2) |
| 1-193 | O | (2) Cl | (4) Cl | H | 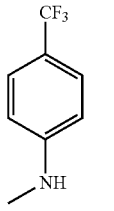 | (I-2) |
| 1-194 | O | (2) Cl | (4) SO$_2$CH$_3$ | H | 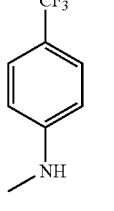 | (I-2) |
| 1-195 | O | (2) Cl | (4) Cl | H | 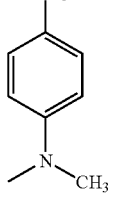 | (I-2) |
| 1-196 | O | (2) Cl | (4) SO$_2$CH$_3$ | H | 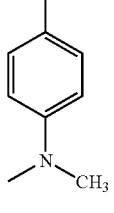 | (I-2) |

TABLE 1-1-continued

Examples of compounds of the formula (I)
Here, $R^1$ and $R^2$ each represent hydrogen and Y represents hydroxyl.

| Ex. No. | Q | (position) $R^3$ | (position) $R^4$ | $R^5$ | Z | Formula physical data |
|---|---|---|---|---|---|---|
| 1-197 | O | (2) Cl | (4) Cl | H | -CH$_2$-N(C=O)N(CH$_3$)-N=N (tetrazolinone, N-CH$_3$) | (I-2) Fp.: 195° C. |
| 1-198 | O | (2) Cl | (4) Cl | CH$_3$ | -CH$_2$-N(C=O)N(CH$_3$)-N=N | (I-2) |
| 1-190 | O | (2) Cl | (4) Cl | H | -CH$_2$-tetrazole | (I-2) |
| 1-200 | O | (2) Cl | (4) Cl | H | -CH$_2$-tetrazole (isomer) | (I-2) |
| 1-201 | O | (2) Cl | (4) Cl | CH$_3$ | -CH$_2$-tetrazole | (I-2) |
| 1-202 | O | (2) Cl | (4) Cl | CH$_3$ | -CH$_2$-tetrazole (isomer) | (I-2) |
| 1-203 | O | (2) Cl | (4) SO$_2$CH$_3$ | H | -CH$_2$-N(C=O)N(CH$_3$)-N=N | (I-2) |
| 1-204 | O | (2) Cl | (4) SO$_2$CH$_3$ | CH$_3$ | -CH$_2$-N(C=O)N(CH$_3$)-N=N | (I-2) |
| 1-205 | O | (2) Cl | (4) SO$_2$CH$_3$ | H | -CH$_2$-tetrazole | (I-2) |
| 1-206 | O | (2) Cl | (4) SO$_2$CH$_3$ | H | -CH$_2$-tetrazole (isomer) | (I-2) |
| 1-207 | O | (2) Cl | (4) SO$_2$CH$_3$ | CH$_3$ | -CH$_2$-tetrazole | (I-2) |

TABLE 1-1-continued

Examples of compounds of the formula (I)
Here, R¹ and R² each represent hydrogen and Y represents hydroxyl.

| Ex. No. | Q | (position) R³ | (position) R⁴ | R⁵ | Z | Formula physical data |
|---|---|---|---|---|---|---|
| 1-208 | O | (2) Cl | (4) SO₂CH₃ | CH₃ | 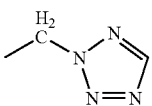 | (I-2) |

TABLE 1-2

Examples of compounds of the formula (I).
Here, in each case R¹ represents methyl in the 4-position,
R² represents methyl in the 4-position and Y represents hydroxyl.

| Ex. No. | Q | (position) R³ | (position) R⁴ | R⁵ | Z | Formula physical data |
|---|---|---|---|---|---|---|
| 2-1 | O | (2) Cl | (4) Cl | H | $\underset{\text{CH}_3}{\overset{\text{OCH}_3}{\diagup\text{N}\diagdown}}$ | (I-2) logP = 2.61[a] |
| 2-2 | O | (2) Cl | (4) Cl | H | morpholino | (I-2) |
| 2-3 | O | (2) Cl | (4) Cl | H | $\diagup\overset{\text{H}}{\text{N}}\diagdown\text{N(CH}_3)_2$ | (I-2) |
| 2-4 | O | (2) Cl | (4) Cl | H | N(C₂H₅)₂ | (I-2) |
| 2-5 | O | (2) Cl | (4) Cl | H | NHCH₃ | (I-2) |
| 2-6 | O | (2) Cl | (4) Cl | H | NHC₂H₅ | (I-2) |
| 2-7 | O | (2) Cl | (4) Cl | H | N(CH₃)₂ | (I-2) |
| 2-8 | O | (2) Cl | (4) Cl | H | 4-methylpiperazin-1-yl | (I-2) |
| 2-9 | O | (2) Cl | (4) Cl | H | NHC₃H₇-i | (I-2) |
| 2-10 | O | (2) Cl | (4) Cl | H | cyclopropyl-NH | (I-2) |
| 2-11 | O | (2) Cl | (4) Cl | H | cyclopentyl-NH | (I-2) |
| 2-12 | O | (2) Cl | (4) Cl | H | cyclohexyl-NH | (I-2) |
| 2-13 | O | (2) Cl | (4) Cl | H | pyrrolidin-1-yl | (I-2) |

TABLE 1-2-continued

Examples of compounds of the formula (I).
Here, in each case R¹ represents methyl in the 4-position,
R² represents methyl in the 4-position and Y represents hydroxyl.

| Ex. No. | Q | (position) R³ | (position) R⁴ | R⁵ | Z | Formula physical data |
|---|---|---|---|---|---|---|
| 2-14 | O | (2) Cl | (4) Cl | H | 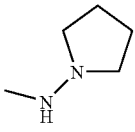 | (I-2) |
| 2-15 | O | (2) Cl | (4) Cl | H | 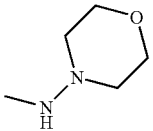 | (I-2) |
| 2-16 | O | (2) Cl | (4) Cl | H | 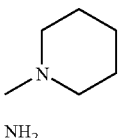 | (I-2) |
| 2-17 | O | (2) Cl | (4) Cl | H | $NH_2$ | (I-2) |
| 2-18 | O | (2) Cl | (4) Cl | H | $NHC_3H_7$-n | (I-2) |
| 2-19 | O | (2) Cl | (4) Cl | H | 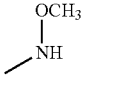 | (I-2) |
| 2-20 | O | (2) Cl | (4) Cl | H | $N(C_3H_7$-n$)_2$ | (I-2) |
| 2-21 | O | (2) Cl | (4) Cl | H | 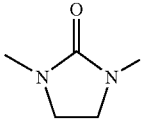 | (I-3) |
| 2-22 | O | (2) Cl | (4) Cl | H | 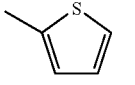 | (I-2) |
| 2-23 | O | (2) Cl | (4) Cl | H | 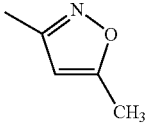 | (I-2) |
| 2-24 | O | (2) Cl | (4) Cl | H | $C_2H_5$ | (I-2) |
| 2-25 | O | (2) Cl | (4) Cl | H | $CH_2OCH_3$ | (I-2) |
| 2-26 | O | (2) Cl | (4) Cl | H | $C_3H_7$-n | (I-2) |
| 2-27 | O | (2) Cl | (4) Cl | H | $C_3H_7$-i | (I-2) |
| 2-28 | O | (2) Cl | (4) Cl | H | $C_4H_9$-n | (I-2) |
| 2-29 | O | (2) Cl | (4) Cl | H | $C_4H_9$-i | (I-2) |
| 2-30 | O | (2) Cl | (4) Cl | H | $C_4H_9$-s | (I-2) |
| 2-30 | O | (2) Cl | (4) Cl | H | $C_4H_9$-t | (I-2) |
| 2-31 | O | (2) Cl | (4) Cl | H | $CH_2Cl$ | (I-2) |
| 2-32 | O | (2) Cl | (4) Cl | H | $CHCl_2$ | (I-2) |
| 2-33 | O | (2) Cl | (4) Cl | H | $CCl_3$ | (I-2) |
| 2-34 | O | (2) Cl | (4) Cl | H | $CF_3$ | (I-2) |
| 2-35 | O | (2) Cl | (4) Cl | H |  | (I-2) |
| 2-36 | O | (2) Cl | (4) Cl | H | 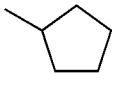 | (I-2) |

TABLE 1-2-continued

Examples of compounds of the formula (I).
Here, in each case $R^1$ represents methyl in the 4-position,
$R^2$ represents methyl in the 4-position and Y represents hydroxyl.

| Ex. No. | Q | (position) $R^3$ | (position) $R^4$ | $R^5$ | Z | Formula physical data |
|---|---|---|---|---|---|---|
| 2-37 | O | (2) Cl | (4) Cl | H | cyclohexyl-CH₂– | (I-2) |
| 2-38 | O | (2) Cl | (4) Cl | H | phenyl-CH₂– | (I-2) |
| 2-39 | O | (2) Cl | (4) Cl | H | phenyl-CH₂CH₂– | (I-2) |
| 2-40 | O | (2) Cl | (4) Cl | H | CH₃O-CH₂-CH₂-NH-CH₂– | (I-2) |
| 2-41 | O | (2) Cl | (4) Cl | H | CH₃O-CH₂-CH₂-NH-CH₂– | (I-2) |
| 2-42 | O | (2) Cl | (4) Cl | H | CH₃O-CH₂-CH₂-N(CH₃)-CH₂– | (I-2) |
| 2-43 | O | (2) Cl | (4) Cl | H | CH₃O-CH₂-CH₂-N(CH₃)-CH₂– | (I-2) |
| 2-44 | O | (2) Cl | (4) Cl | H | (CH₃O-CH₂-CH₂-)₂N-CH₂– | (I-2) |

TABLE 1-2-continued

Examples of compounds of the formula (I).
Here, in each case R¹ represents methyl in the 4-position,
R² represents methyl in the 4-position and Y represents hydroxyl.

| Ex. No. | Q | (position) R³ | (position) R⁴ | R⁵ | Z | Formula physical data |
|---|---|---|---|---|---|---|
| 2-45 | O | (2) Cl | (4) Cl | H | OH–NH– | (I-2) |
| 2-46 | O | (2) Cl | (4) Cl | H | OC₂H₅–NH– | (I-2) |
| 2-47 | O | (2) Cl | (4) Cl | H | OC₃H₇-n–NH– | (I-2) |
| 2-48 | O | (2) Cl | (4) Cl | H | OC₃H₇-i–NH– | (I-2) |
| 2-49 | O | (2) Cl | (4) Cl | H | HC=CH₂–CH₂–O–NH– | (I-2) |
| 2-50 | O | (2) Cl | (4) Cl | H | CH₂=CH–CH₂–NH– | (I-2) |
| 2-51 | O | (2) Cl | (4) Cl | H | C₆H₅–NH– | (I-2) |
| 2-52 | O | (2) Cl | (4) Cl | H | C₆H₅–CH₂–NH– | (I-2) |
| 2-53 | O | (2) Cl | (4) Cl | H | C₆H₅–CH₂–O–NH– | (I-2) |
| 2-54 | O | (2) Cl | (4) Cl | H | 3-isoxazolyl | (I-2) |

TABLE 1-2-continued

Examples of compounds of the formula (I).
Here, in each case R¹ represents methyl in the 4-position,
R² represents methyl in the 4-position and Y represents hydroxyl.

| Ex. No. | Q | (position) R³ | (position) R⁴ | R⁵ | Z | Formula physical data |
|---|---|---|---|---|---|---|
| 2-55 | O | (2) Cl | (4) Cl | H | 3-methylisoxazoline | (I-2) |
| 2-56 | O | (2) Cl | (4) Cl | H | 3-methylpyridine | (I-2) |
| 2-57 | O | (2) Cl | (4) Cl | H | 2-methylfuran | (I-2) |
| 2-58 | O | (2) Cl | (4) Cl | H | 2-chloro-methylbenzene | (I-2) |
| 2-59 | O | (2) Cl | (4) Cl | H | 3-chloro-methylbenzene | (I-2) |
| 2-60 | O | (2) Cl | (4) Cl | H | 4-chloro-methylbenzene | (I-2) |
| 2-61 | O | (2) Cl | (4) Cl | H | isoxazolidin-2-ylmethyl | (I-2) logP = 2.57[a] |
| 2-62 | O | (2) Cl | (4) SO₂CH₃ | H | isoxazolidin-2-ylmethyl | (I-2) |
| 2-63 | O | (4) CF₃ | — | H | isoxazolidin-2-ylmethyl | (I-1) |
| 2-64 | O | (2) OCH₃ | — | H | isoxazolidin-2-ylmethyl | (I-3) |
| 2-65 | O | (2) NO₂ | — | H | isoxazolidin-2-ylmethyl | (I-3) |
| 2-66 | O | (4) CF₃ | — | H | N(OCH₃)(CH₃)-methyl | (I-1) |
| 2-67 | O | (2) OCH₃ | — | H | N(OCH₃)(CH₃)-methyl | (I-3) |

TABLE 1-2-continued

Examples of compounds of the formula (I).
Here, in each case $R^1$ represents methyl in the 4-position,
$R^2$ represents methyl in the 4-position and Y represents hydroxyl.

| Ex. No. | Q | (position) $R^3$ | (position) $R^4$ | $R^5$ | Z | Formula physical data |
|---|---|---|---|---|---|---|
| 2-68 | O | (2) NO$_2$ | — | H | N(OCH$_3$)(CH$_3$) | (I-3) |
| 2-69 | O | (2) Cl | (4) Cl | H | 1,2-oxazinane (N,O 6-ring) | (I-2) logP = 2.83[a] |
| 2-70 | O | (2) Cl | (4) SO$_2$CH$_3$ | H | 1,2-oxazinane (N,O 6-ring) | (I-2) |
| 2-71 | O | (2) Cl | (4) SO$_2$CH$_3$ | H | pyrrolidin-1-yl | (I-2) |
| 2-72 | O | (2) Cl | (4) SO$_2$CH$_3$ | H | NH(OCH$_3$) | (I-2) |
| 2-73 | O | (2) Cl | (4) SO$_2$CH$_3$ | H | 4,5-dihydroisoxazol-3-yl | (I-2) |
| 2-74 | O | (2) Cl | (4) SO$_2$CH$_3$ | H | furan-2-yl | (I-2) |

TABLE 1-3

Examples of compounds of formula (I)
Here, in each case $R^1$ represents methyl in the 5-position,
$R^2$ represents hydrogen and Y represents hydroxyl.

| Ex. No. | Q | (position) $R^3$ | (position) $R^4$ | $R^5$ | Z | Formula physical data |
|---|---|---|---|---|---|---|
| 3-1 | O | (2) Cl | (4) Cl | H | N(OCH$_3$)(CH$_3$) | (I-2) logP = 2.33[a] |
| 3-2 | O | (2) Cl | (4) Cl | H | morpholin-4-yl | (I-2) |
| 3-3 | O | (2) Cl | (4) Cl | H | N(CH$_3$)N(CH$_3$)$_2$ | (I-2) |
| 3-4 | O | (2) Cl | (4) Cl | H | N(C$_2$H$_5$)$_2$ | (I-2) |
| 3-5 | O | (2) Cl | (4) Cl | H | NHCH$_3$ | (I-2) |
| 3-6 | O | (2) Cl | (4) Cl | H | NHC$_2$H$_5$ | (I-2) |
| 3-7 | O | (2) Cl | (4) Cl | H | N(CH$_3$)$_2$ | (I-2) |
| 3-8 | O | (2) Cl | (4) Cl | H | 4-methylpiperazin-1-yl (N-CH$_3$) | (I-2) |
| 3-9 | O | (2) Cl | (4) Cl | H | NHC$_3$H$_7$-i | (I-2) |
| 3-10 | O | (2) Cl | (4) Cl | H | NH-cyclopropyl | (I-2) |

TABLE 1-3-continued

Examples of compounds of formula (I)
Here, in each case R¹ represents methyl in the 5-position,
R² represents hydrogen and Y represents hydroxyl.

| Ex. No. | Q | (position) R³ | (position) R⁴ | R⁵ | Z | Formula physical data |
|---|---|---|---|---|---|---|
| 3-11 | O | (2) Cl | (4) Cl | H | 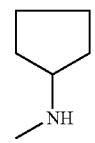 | (I-2) |
| 3-12 | O | (2) Cl | (4) Cl | H | 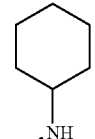 | (I-2) |
| 3-13 | O | (2) Cl | (4) Cl | H | 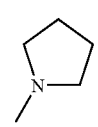 | (I-2) |
| 3-14 | O | (2) Cl | (4) Cl | H | 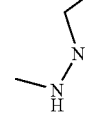 | (I-2) |
| 3-15 | O | (2) Cl | (4) Cl | H | 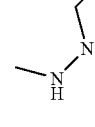 | (I-2) |
| 3-16 | O | (2) Cl | (4) Cl | H | 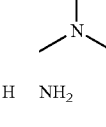 | (I-2) |
| 3-17 | O | (2) Cl | (4) Cl | H | $NH_2$ | (I-2) |
| 3-18 | O | (2) Cl | (4) Cl | H | $NHC_3H_7$-n | (I-2) |
| 3-19 | O | (2) Cl | (4) Cl | H |  | (I-2) |
| 3-20 | O | (2) Cl | (4) Cl | H | $N(C_3H_7$-n$)_2$ | (I-2) |
| 3-21 | O | (2) Cl | (4) Cl | H |  | (I-3) |
| 3-22 | O | (2) Cl | (4) Cl | H |  | (I-2) |
| 3-23 | O | (2) Cl | (4) Cl | H | 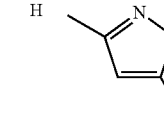 | (I-2) |
| 3-24 | O | (2) Cl | (4) Cl | H | $C_2H_5$ | (I-2) |
| 3-25 | O | (2) Cl | (4) Cl | H | $CH_2OCH_3$ | (I-2) |
| 3-26 | O | (2) Cl | (4) Cl | H | $C_3H_7$-n | (I-2) |
| 3-27 | O | (2) Cl | (4) Cl | H | $C_3H_7$-i | (I-2) |
| 3-28 | O | (2) Cl | (4) Cl | H | $C_4H_9$-n | (I-2) |
| 3-29 | O | (2) Cl | (4) Cl | H | $C_4H_9$-i | (I-2) |
| 3-30 | O | (2) Cl | (4) Cl | H | $C_4H_9$-s | (I-2) |
| 3-30 | O | (2) Cl | (4) Cl | H | $C_4H_9$-t | (I-2) |
| 3-31 | O | (2) Cl | (4) Cl | H | $CH_2Cl$ | (I-2) |
| 3-32 | O | (2) Cl | (4) Cl | H | $CHCl_2$ | (I-2) |
| 3-33 | O | (2) Cl | (4) Cl | H | $CCl_3$ | (I-2) |
| 3-34 | O | (2) Cl | (4) Cl | H | $CF_3$ | (I-2) |
| 3-35 | O | (2) Cl | (4) Cl | H |  | (I-2) |
| 3-36 | O | (2) Cl | (4) Cl | H |  | (I-2) |
| 3-37 | O | (2) Cl | (4) Cl | H |  | (I-2) |
| 3-38 | O | (2) Cl | (4) Cl | H |  | (I-2) |
| 3-39 | O | (2) Cl | (4) Cl | H |  | (I-2) |
| 3-40 | O | (2) Cl | (4) Cl | H |  | (I-2) |

TABLE 1-3-continued

Examples of compounds of formula (I)
Here, in each case R¹ represents methyl in the 5-position,
R² represents hydrogen and Y represents hydroxyl.

| Ex. No. | Q | (position) R³ | (position) R⁴ | R⁵ | Z | Formula physical data |
|---|---|---|---|---|---|---|
| 3-41 | O | (2) Cl | (4) Cl | H | 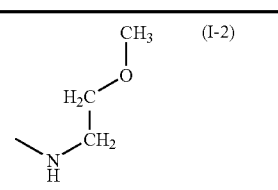 | (I-2) |
| 3-42 | O | (2) Cl | (4) Cl | H | 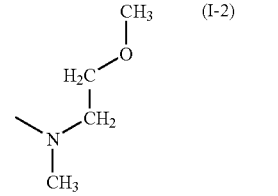 | (I-2) |
| 3-43 | O | (2) Cl | (4) Cl | H | 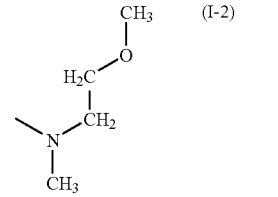 | (I-2) |
| 3-44 | O | (2) Cl | (4) Cl | H | 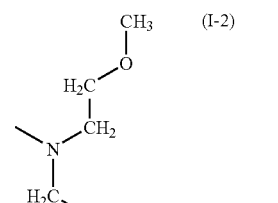 | (I-2) |
| 3-45 | O | (2) Cl | (4) Cl | H | OH<br>NH | (I-2) |
| 3-46 | O | (2) Cl | (4) Cl | H | OC₂H₅<br>NH | (I-2) |
| 3-47 | O | (2) Cl | (4) Cl | H | OC₃H₇-n<br>NH | (I-2) |
| 3-48 | O | (2) Cl | (4) Cl | H | OC₃H₇-i<br>NH | (I-2) |
| 3-49 | O | (2) Cl | (4) Cl | H | 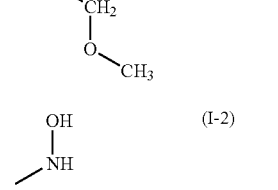 | (I-2) |
| 3-50 | O | (2) Cl | (4) Cl | H | 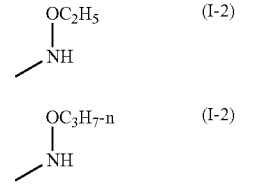 | (I-2) |
| 3-51 | O | (2) Cl | (4) Cl | H | 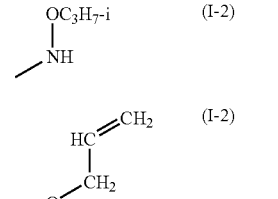 | (I-2) |
| 3-52 | O | (2) Cl | (4) Cl | H | 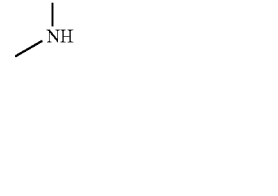 | (I-2) |
| 3-53 | O | (2) Cl | (4) Cl | H | 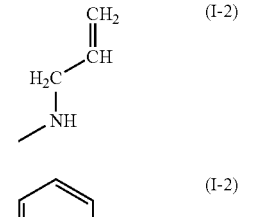 | (I-2) |
| 3-54 | O | (2) Cl | (4) Cl | H | 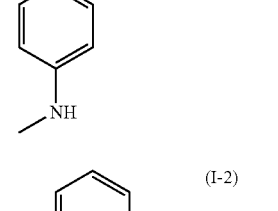 | (I-2) |
| 3-55 | O | (2) Cl | (4) Cl | H | 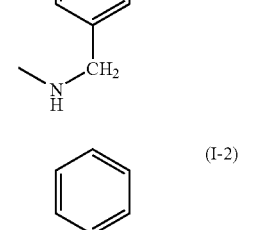 | (I-2) |
| 3-56 | O | (2) Cl | (4) Cl | H | 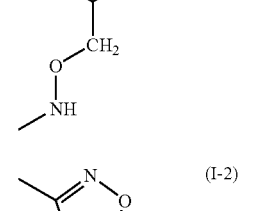 | (I-2) |
| 3-57 | O | (2) Cl | (4) Cl | H | 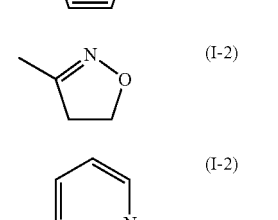 | (I-2) |
| 3-58 | O | (2) Cl | (4) Cl | H | 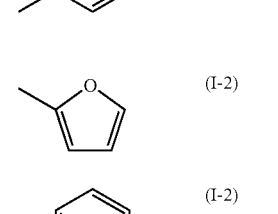 | (I-2) |

TABLE 1-3-continued

Examples of compounds of formula (I)
Here, in each case $R^1$ represents methyl in the 5-position,
$R^2$ represents hydrogen and Y represents hydroxyl.

| Ex. No. | Q | (position) $R^3$ | (position) $R^4$ | $R^5$ | Z | Formula physical data |
|---|---|---|---|---|---|---|
| 3-59 | O | (2) Cl | (4) Cl | H | 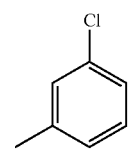 | (I-2) |
| 3-60 | O | (2) Cl | (4) Cl | H | 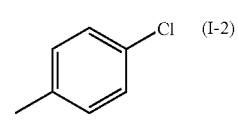 | (I-2) |
| 3-61 | O | (2) Cl | (4) Cl | H | 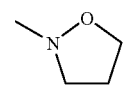 | (I-2) logP = 2.25[a)] |
| 3-62 | O | (2) Cl | (4) SO$_2$CH$_3$ | H | 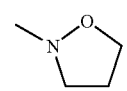 | (I-2) |
| 3-62 | O | (4) CF$_3$ | — | H | 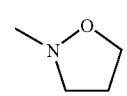 | (I-1) |
| 3-64 | O | (2) OCH$_3$ | — | H | 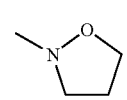 | (I-3) |
| 3-65 | O | (2) NO$_2$ | — | H | 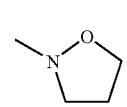 | (I-3) |
| 3-66 | O | (4) CF$_3$ | — | H | 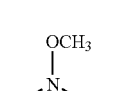 | (I-1) |
| 3-67 | O | (2) OCH$_3$ | — | H | 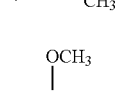 | (I-3) |
| 3-68 | O | (2) NO$_2$ | — | H | 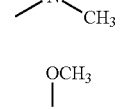 | (I-3) |
| 3-69 | O | (2) Cl | (4) Cl | H | 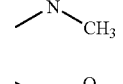 | (I-2) logP = 2.52[a)] |
| 3-70 | O | (2) Cl | (4) SO$_2$CH$_3$ | H | 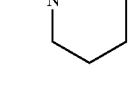 | (I-2) |
| 3-71 | O | (2) Cl | (4) SO$_2$CH$_3$ | H | 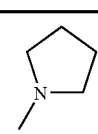 | (I-2) |
| 3-72 | O | (2) Cl | (4) SO$_2$CH$_3$ | H |  | (I-2) |
| 3-73 | O | (2) Cl | (4) SO$_2$CH$_3$ | H |  | (I-2) |
| 3-74 | O | (2) Cl | (4) SO$_2$CH$_3$ | H | 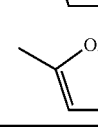 | (I-2) |

TABLE 1-4

Examples of compounds of the formula (I)
Here, in each case $R^1$ represents methyl in the 5-position,
$R^2$ represents methyl in the 5-position and Y represents hydroxyl.

| Ex. No. | Q | (position) $R^3$ | (position) $R^4$ | $R^5$ | Z | Formula physical data |
|---|---|---|---|---|---|---|
| 4-1 | O | (2) Cl | (4) Cl | H | 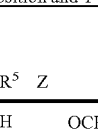 | (I-2) logP = 2.54[a)] |
| 4-2 | O | (2) Cl | (4) Cl | H | 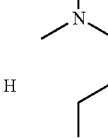 | (I-2) |
| 4-3 | O | (2) Cl | (4) Cl | H |  | (I-2) |
| 4-4 | O | (2) Cl | (4) Cl | H | N(C$_2$H$_5$)$_2$ | (I-2) |
| 4-5 | O | (2) Cl | (4) Cl | H | NHCH$_3$ | (I-2) |
| 4-6 | O | (2) Cl | (4) Cl | H | NHC$_2$H$_5$ | (I-2) |
| 4-7 | O | (2) Cl | (4) Cl | H | N(CH$_3$)$_2$ | (I-2) |
| 4-8 | O | (2) Cl | (4) Cl | H |  | (I-2) |
| 4-9 | O | (2) Cl | (4) Cl | H | NHC$_3$H$_7$-i | (I-2) |
| 4-10 | O | (2) Cl | (4) Cl | H |  | (I-2) |

TABLE 1-4-continued

Examples of compounds of the formula (I)
Here, in each case R¹ represents methyl in the 5-position,
R² represents methyl in the 5-position and Y represents hydroxyl.

| Ex. No. | Q | (position) $R^3$ | (position) $R^4$ | $R^5$ | Z | Formula physical data |
|---|---|---|---|---|---|---|
| 4-11 | O | (2) Cl | (4) Cl | H | cyclopentyl-NH- | (I-2) |
| 4-12 | O | (2) Cl | (4) Cl | H | cyclohexyl-NH- | (I-2) |
| 4-13 | O | (2) Cl | (4) Cl | H | pyrrolidin-1-yl | (I-2) |
| 4-14 | O | (2) Cl | (4) Cl | H | pyrrolidin-1-yl-NH- | (I-2) |
| 4-15 | O | (2) Cl | (4) Cl | H | morpholin-4-yl-NH- | (I-2) |
| 4-16 | O | (2) Cl | (4) Cl | H | piperidin-1-yl | (I-2) |
| 4-17 | O | (2) Cl | (4) Cl | H | NH₂ | (I-2) |
| 4-18 | O | (2) Cl | (4) Cl | H | NHC₃H₇-n | (I-2) |
| 4-19 | O | (2) Cl | (4) Cl | H | CH₃O-NH- | (I-2) |
| 4-20 | O | (2) Cl | (4) Cl | H | N(C₃H₇-n)₂ | (I-2) |
| 4-21 | O | (2) Cl | (4) Cl | H | 1,3-dimethyl-2-oxo-imidazolidin-1-yl | (I-3) |
| 4-22 | O | (2) Cl | (4) Cl | H | thien-2-yl | (I-2) |
| 4-23 | O | (2) Cl | (4) Cl | H | 3,5-dimethylisoxazol-4-yl | (I-2) |
| 4-24 | O | (2) Cl | (4) Cl | H | C₂H₅ | (I-2) |
| 4-25 | O | (2) Cl | (4) Cl | H | CH₂OCH₃ | (I-2) |
| 4-26 | O | (2) Cl | (4) Cl | H | C₃H₇-n | (I-2) |
| 4-27 | O | (2) Cl | (4) Cl | H | C₃H₇-i | (I-2) |
| 4-28 | O | (2) Cl | (4) Cl | H | C₄H₉-n | (I-2) |
| 4-29 | O | (2) Cl | (4) Cl | H | C₄H₉-i | (I-2) |
| 4-30 | O | (2) Cl | (4) Cl | H | C₄H₉-s | (I-2) |
| 4-30 | O | (2) Cl | (4) Cl | H | C₄H₉-t | (I-2) |
| 4-31 | O | (2) Cl | (4) Cl | H | CH₂Cl | (I-2) |
| 4-32 | O | (2) Cl | (4) Cl | H | CHCl₂ | (I-2) |
| 4-33 | O | (2) Cl | (4) Cl | H | CCl₃ | (I-2) |
| 4-34 | O | (2) Cl | (4) Cl | H | CF₃ | (I-2) |
| 4-35 | O | (2) Cl | (4) Cl | H | cyclopropyl | (I-2) |
| 4-36 | O | (2) Cl | (4) Cl | H | cyclopentyl | (I-2) |
| 4-37 | O | (2) Cl | (4) Cl | H | cyclohexyl | (I-2) |
| 4-38 | O | (2) Cl | (4) Cl | H | phenyl | (I-2) |
| 4-39 | O | (2) Cl | (4) Cl | H | benzyl | (I-2) |
| 4-40 | O | (2) Cl | (4) Cl | H | CH₃OCH₂CH₂NH- | (I-2) |

TABLE 1-4-continued

Examples of compounds of the formula (I)
Here, in each case R¹ represents methyl in the 5-position,
R² represents methyl in the 5-position and Y represents hydroxyl.

| Ex. No. | Q | (position) R³ | (position) R⁴ | R⁵ | Z | Formula physical data |
|---|---|---|---|---|---|---|
| 4-41 | O | (2) Cl | (4) Cl | H | CH₃-O-CH₂-CH₂-NH-CH₂- (methoxyethyl-N-methyl) | (I-2) |
| 4-42 | O | (2) Cl | (4) Cl | H | CH₃-O-CH₂-CH₂-N(CH₃)-CH₂- | (I-2) |
| 4-43 | O | (2) Cl | (4) Cl | H | CH₃-O-CH₂-CH₂-N(CH₃)-CH₂- | (I-2) |
| 4-44 | O | (2) Cl | (4) Cl | H | bis(2-methoxyethyl)aminomethyl | (I-2) |
| 4-45 | O | (2) Cl | (4) Cl | H | OH-NH-CH₂- | (I-2) |
| 4-46 | O | (2) Cl | (4) Cl | H | OC₂H₅-NH-CH₂- | (I-2) |
| 4-47 | O | (2) Cl | (4) Cl | H | OC₃H₇-n-NH-CH₂- | (I-2) |
| 4-48 | O | (2) Cl | (4) Cl | H | OC₃H₇-i-NH-CH₂- | (I-2) |
| 4-49 | O | (2) Cl | (4) Cl | H | CH₂=CH-CH₂-O-NH-CH₂- | (I-2) |
| 4-50 | O | (2) Cl | (4) Cl | H | CH₂=CH-CH₂-NH-CH₂- | (I-2) |
| 4-51 | O | (2) Cl | (4) Cl | H | C₆H₅-NH-CH₂- | (I-2) |
| 4-52 | O | (2) Cl | (4) Cl | H | C₆H₅-CH₂-NH-CH₂- | (I-2) |
| 4-53 | O | (2) Cl | (4) Cl | H | C₆H₅-CH₂-O-NH-CH₂- | (I-2) |
| 4-54 | O | (2) Cl | (4) Cl | H | 3-methylisoxazol-5-yl | (I-2) |
| 4-55 | O | (2) Cl | (4) Cl | H | 3-methyl-4,5-dihydroisoxazol-5-yl | (I-2) logP = 2.59[a] |
| 4-56 | O | (2) Cl | (4) Cl | H | 3-methylpyridin-5-yl | (I-2) |
| 4-57 | O | (2) Cl | (4) Cl | H | 2-methylfuran-5-yl | (I-2) |
| 4-58 | O | (2) Cl | (4) Cl | H | 2-chloro-6-methylphenyl | (I-2) |

TABLE 1-4-continued

Examples of compounds of the formula (I)
Here, in each case R¹ represents methyl in the 5-position,
R² represents methyl in the 5-position and Y represents hydroxyl.

| Ex. No. | Q | (position) R³ | (position) R⁴ | R⁵ | Z | Formula physical data |
|---|---|---|---|---|---|---|
| 4-59 | O | (2) Cl | (4) Cl | H | 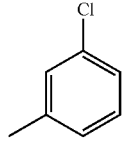 | (I-2) |
| 4-60 | O | (2) Cl | (4) Cl | H | 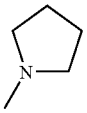 | (I-2) |
| 4-61 | O | (2) Cl | (4) Cl | H | 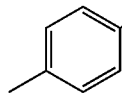 | (I-2) logP = 2.51[a)] |
| 4-62 | O | (2) Cl | (4) SO₂CH₃ | H | 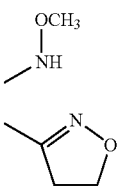 | (I-2) |
| 4-63 | O | (4) CF₃ | — | H | 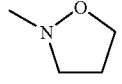 | (I-1) |
| 4-64 | O | (2) OCH₃ | — | H |  | (I-3) |
| 4-65 | O | (2) NO₂ | — | H | 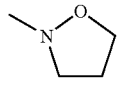 | (I-3) |
| 4-66 | O | (4) CF₃ | — | H |  | (I-1) |
| 4-67 | O | (2) OCH₃ | — | H | 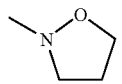 | (I-3) |
| 4-68 | O | (2) NO₂ | — | H | 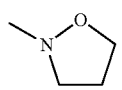 | (I-3) |
| 4-69 | O | (2) Cl | (4) Cl | H | 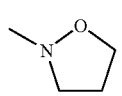 | (I-2) logP = 2.76[a)] |
| 4-70 | O | (2) Cl | (4) SO₂CH₃ | H |  | (I-2) |
| 4-71 | O | (2) Cl | (4) SO₂CH₃ | H | 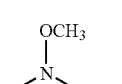 | (I-2) |
| 4-72 | O | (2) Cl | (4) SO₂CH₃ | H |  | (I-2) |
| 4-73 | O | (2) Cl | (4) SO₂CH₃ | H | 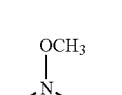 | (I-2) |
| 4-74 | O | (2) Cl | (4) SO₂CH₃ | H |  | (I-2) |

TABLE 1-5

Examples of compounds of the formula (I)
Here, in each case R¹ and R² represent a dimethylene grouping between
positions 4 and 6 - "(4)-CH₂CH₂-(6)" - and Y represents hydroxyl.

| Ex. No. | Q | (position) R³ | (position) R⁴ | R⁵ | Z | Formula physical data |
|---|---|---|---|---|---|---|
| 5-1 | O | (2) Cl | (4) Cl | H | 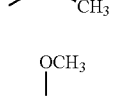 | (I-2) logP = 2.23[a)] |
| 5-2 | O | (2) Cl | (4) Cl | H |  | (I-2) |
| 5-3 | O | (2) Cl | (4) Cl | H | 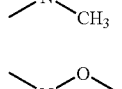 | (I-2) |
| 5-4 | O | (2) Cl | (4) Cl | H | N(C₂H₅)₂ | (I-2) |
| 5-5 | O | (2) Cl | (4) Cl | H | NHCH₃ | (I-2) |
| 5-6 | O | (2) Cl | (4) Cl | H | NHC₂H₅ | (I-2) |
| 5-7 | O | (2) Cl | (4) Cl | H | N(CH₃)₂ | (I-2) |
| 5-8 | O | (2) Cl | (4) Cl | H |  | (I-2) |
| 5-9 | O | (2) Cl | (4) Cl | H | NHC₃H₇-i | (I-2) |
| 5-10 | O | (2) Cl | (4) Cl | H | 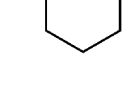 | (I-2) |

TABLE 1-5-continued

Examples of compounds of the formula (I)
Here, in each case R$^1$ and R$^2$ represent a dimethylene grouping between positions 4 and 6 - "(4)-CH$_2$CH$_2$-(6)" - and Y represents hydroxyl.

| Ex. No. | Q | (position) R$^3$ | (position) R$^4$ | R$^5$ | Z | Formula physical data |
|---|---|---|---|---|---|---|
| 5-11 | O | (2) Cl | (4) Cl | H | cyclopentyl-NH- | (I-2) |
| 5-12 | O | (2) Cl | (4) Cl | H | cyclohexyl-NH- | (I-2) |
| 5-13 | O | (2) Cl | (4) Cl | H | pyrrolidinyl | (I-2) |
| 5-14 | O | (2) Cl | (4) Cl | H | pyrrolidin-1-yl-NH- | (I-2) |
| 5-15 | O | (2) Cl | (4) Cl | H | morpholin-4-yl-NH- | (I-2) |
| 5-16 | O | (2) Cl | (4) Cl | H | piperidin-1-yl | (I-2) |
| 5-17 | O | (2) Cl | (4) Cl | H | NH$_2$ | (I-2) |
| 5-18 | O | (2) Cl | (4) Cl | H | NHC$_3$H$_7$-n | (I-2) |
| 5-19 | O | (2) Cl | (4) Cl | H | -NH-OCH$_3$ | (I-2) |
| 5-20 | O | (2) Cl | (4) Cl | H | N(C$_3$H$_7$-n)$_2$ | (I-2) |
| 5-21 | O | (2) Cl | (4) Cl | H | 1,3-dimethyl-2-oxoimidazolidin-yl | (I-3) |
| 5-22 | O | (2) Cl | (4) Cl | H | thien-2-yl | (I-2) |
| 5-23 | O | (2) Cl | (4) Cl | H | 3-methyl-5-methylisoxazolyl | (I-2) |
| 5-24 | O | (2) Cl | (4) Cl | H | C$_2$H$_5$ | (I-2) |
| 5-25 | O | (2) Cl | (4) Cl | H | CH$_2$OCH$_3$ | (I-2) |
| 5-26 | O | (2) Cl | (4) Cl | H | C$_3$H$_7$-n | (I-2) |
| 5-27 | O | (2) Cl | (4) Cl | H | C$_3$H$_7$-i | (I-2) |
| 5-28 | O | (2) Cl | (4) Cl | H | C$_4$H$_9$-n | (I-2) |
| 5-29 | O | (2) Cl | (4) Cl | H | C$_4$H$_9$-i | (I-2) |
| 5-30 | O | (2) Cl | (4) Cl | H | C$_4$H$_9$-s | (I-2) |
| 5-30 | O | (2) Cl | (4) Cl | H | C$_4$H$_9$-t | (I-2) |
| 5-31 | O | (2) Cl | (4) Cl | H | CH$_2$Cl | (I-2) |
| 5-32 | O | (2) Cl | (4) Cl | H | CHCl$_2$ | (I-2) |
| 5-33 | O | (2) Cl | (4) Cl | H | CCl$_3$ | (I-2) |
| 5-34 | O | (2) Cl | (4) Cl | H | CF$_3$ | (I-2) |
| 5-35 | O | (2) Cl | (4) Cl | H | cyclopropyl | (I-2) |
| 5-36 | O | (2) Cl | (4) Cl | H | cyclopentyl | (I-2) |
| 5-37 | O | (2) Cl | (4) Cl | H | cyclohexyl | (I-2) |
| 5-38 | O | (2) Cl | (4) Cl | H | phenyl | (I-2) |
| 5-39 | O | (2) Cl | (4) Cl | H | benzyl (CH$_2$-phenyl) | (I-2) |
| 5-40 | O | (2) Cl | (4) Cl | H | -NH-CH$_2$-CH$_2$-O-CH$_3$ | (I-2) |

TABLE 1-5-continued

Examples of compounds of the formula (I)
Here, in each case $R^1$ and $R^2$ represent a dimethylene grouping between positions 4 and 6 - "(4)-CH$_2$CH$_2$-(6)" - and Y represents hydroxyl.

| Ex. No. | Q | (position) $R^3$ | (position) $R^4$ | $R^5$ | Z | Formula physical data |
|---|---|---|---|---|---|---|
| 5-41 | O | (2) Cl | (4) Cl | H | CH$_3$OCH$_2$CH$_2$-NH- | (I-2) |
| 5-42 | O | (2) Cl | (4) Cl | H | CH$_3$OCH$_2$CH$_2$-N(CH$_3$)- | (I-2) |
| 5-43 | O | (2) Cl | (4) Cl | H | CH$_3$OCH$_2$CH$_2$-N(CH$_3$)- | (I-2) |
| 5-44 | O | (2) Cl | (4) Cl | H | N(CH$_2$CH$_2$OCH$_3$)$_2$- | (I-2) |
| 5-45 | O | (2) Cl | (4) Cl | H | HO-NH- | (I-2) |
| 5-46 | O | (2) Cl | (4) Cl | H | C$_2$H$_5$O-NH- | (I-2) |
| 5-47 | O | (2) Cl | (4) Cl | H | n-C$_3$H$_7$O-NH- | (I-2) |
| 5-48 | O | (2) Cl | (4) Cl | H | i-C$_3$H$_7$O-NH- | (I-2) |
| 5-49 | O | (2) Cl | (4) Cl | H | CH$_2$=CH-CH$_2$-O-NH- | (I-2) |
| 5-50 | O | (2) Cl | (4) Cl | H | CH$_2$=CH-CH$_2$-NH- | (I-2) |
| 5-51 | O | (2) Cl | (4) Cl | H | Ph-NH- | (I-2) |
| 5-52 | O | (2) Cl | (4) Cl | H | Ph-CH$_2$-NH- | (I-2) |
| 5-53 | O | (2) Cl | (4) Cl | H | Ph-CH$_2$-O-NH- | (I-2) |
| 5-54 | O | (2) Cl | (4) Cl | H | isoxazol-3-yl | (I-2) |
| 5-55 | O | (2) Cl | (4) Cl | H | 4,5-dihydroisoxazol-3-yl | (I-2) |
| 5-56 | O | (2) Cl | (4) Cl | H | pyridin-3-yl | (I-2) |
| 5-57 | O | (2) Cl | (4) Cl | H | furan-2-yl | (I-2) |
| 5-58 | O | (2) Cl | (4) Cl | H | 2-chlorophenyl | (I-2) |

TABLE 1-5-continued

Examples of compounds of the formula (I)
Here, in each case R¹ and R² represent a dimethylene grouping between positions 4 and 6 - "(4)-CH₂CH₂-(6)" - and Y represents hydroxyl.

| Ex. No. | Q | (position) R³ | (position) R⁴ | R⁵ | Z | Formula physical data |
|---|---|---|---|---|---|---|
| 5-59 | O | (2) Cl | (4) Cl | H | | (I-2) |
| 5-60 | O | (2) Cl | (4) Cl | H | | (I-2) |
| 5-61 | O | (2) Cl | (4) Cl | H | | (I-2) |
| 5-62 | O | (2) Cl | (4) SO₂CH₃ | H | | (I-2) |
| 5-63 | O | (4) CF₃ | — | H | | (I-1) |
| 5-64 | O | (2) OCH₃ | — | H | | (I-3) |
| 5-65 | O | (2) NO₂ | — | H | | (I-3) |
| 5-66 | O | (4) CF₃ | — | H | OCH₃ / N / CH₃ | (I-1) |
| 5-67 | O | (2) OCH₃ | — | H | OCH₃ / N / CH₃ | (I-3) |
| 5-68 | O | (2) NO₂ | — | H | OCH₃ / N / CH₃ | (I-3) |
| 5-69 | O | (2) Cl | (4) Cl | H | | (I-2) |
| 5-70 | O | (2) Cl | (4) SO₂CH₃ | H | | (I-2) |
| 5-71 | O | (2) Cl | (4) SO₂CH₃ | H | | (I-2) |
| 5-72 | O | (2) Cl | (4) SO₂CH₃ | H | OCH₃ / NH | (I-2) |
| 5-73 | O | (2) Cl | (4) SO₂CH₃ | H | | (I-2) |
| 5-74 | O | (2) Cl | (4) SO₂CH₃ | H | | (I-2) |
| 5-75 | O | (2) Cl | (4) SO₂CH₃ | H | OCH₃ / N / CH₃ | (I-2) |

The log P values given in Tables 1-1, 1-2, 1-3, 1-4 were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding measurement results are marked [a)] in Table 1.

(b) Mobile phases for the determination in the neutral range: 0.01 molar aqueous phosphate buffer solution, acetonitrile; linear gradient from 10% acetonitrile to 90% acetonitrile—the corresponding measurement results are marked [b)] in Table 1.

Calibration was carried out using unbranched alkan-2-ones (having from 3 to 16 carbon atoms) with known log P values (the log P values were determined by the retention times using linear interpolation between two successive alkanones).

The lambda max values were determined in the maxima of the chromatographic signals using the UV spectra from 200 nm to 400 nm.

Starting Materials of the Formula (III):

Example (III-1)

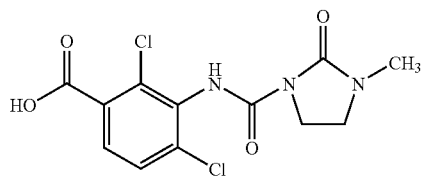

A mixture of 11.3 g (32.9 mmol) of methyl 2,4-dichloro-3-[[(3-methyl-2-oxo-1-imidazolidinyl)-carbonyl]-amino]-benzoate, 50 ml of water, 50 ml of tetrahydrofuran and 1.3 g of sodium hydroxide is stirred at room temperature (about 20° C.) for 18 hours and then concentrated under reduced pressure to about half the original volume. The mixture is then extracted with diethyl ether, the organic phase is separated off (and discarded) and the aqueous phase is acidified with conc. hydrochloric acid. The resulting crystalline product is isolated by filtration with suction.

This gives 9.1 g (81.5% of theory) of 2,4-dichloro-3-[[(3-methyl-2-oxo-1-imidazolidinyl)-carbonyl]-amino]-benzoic acid.

log P (pH=2.3): 1.35.

Analogously to Example (III-1), it is also possible to prepare, for example, the compounds of the general formula (III) listed in Table 2 below.

TABLE 2

Examples of the compounds of the formula (III)

| Ex. No. | (position) R³ | (position) R⁴ | R⁵ | physical data |
|---------|---------------|---------------|-----|---------------|
| III-2 | (2) Cl | (4) Cl | (3) [H₃C-N-OCH₃ group with urea linker] | logP = 1.17ᵃ⁾ |
| III-3 | (2) Cl | (4) Cl | (3) [imidazolidinone with C₃H₇-i] | |
| III-4 | (2) Cl | (4) Cl | (3) [tetrahydropyrimidinone with CH₃] | logP = 1.58ᵃ⁾ |
| III-5 | (2) Cl | (4) Cl | (3) [imidazolidinone with C₂H₅] | |
| III-6 | (2) Cl | (4) Cl | (3) [morpholine carbonyl] | logP = 0.78ᵃ⁾ |
| III-7 | (2) Cl | (4) Cl | (3) [H-N-N(CH₃)₂ urea] | logP = 1.05ᵃ⁾ |
| III-8 | (2) Cl | (4) Cl | (3) [N-methylpiperazine carbonyl] | |
| III-9 | (2) Cl | (4) Cl | (3) [N(C₂H₅)₂ urea] | logP = 1.50ᵃ⁾ |

TABLE 2-continued

Examples of the compounds of the formula (III)

| Ex. No. | (position) R³ | (position) R⁴ | (position) R⁵ | physical data |
|---|---|---|---|---|
| III-10 | (4) Cl | — | (2) H₃C-N(OCH₃)-C(=O)-NH-CH₃ | logP = 2.43[a] |
| III-11 | (4) CF₃ | — | (2) 1-methyl-2-oxo-imidazolidin-3-yl-C(=O)-NH-CH₃ | logP = 2.13[a] |
| III-12 | (4) CF₃ | — | (2) 1-methyl-2-oxo-tetrahydropyrimidin-3-yl-C(=O)-NH-CH₃ | |
| III-13 | (4) CF₃ | — | (2) 1-ethyl-2-oxo-imidazolidin-3-yl-C(=O)-NH-CH₃ | |
| III-14 | (4) CF₃ | — | (2) morpholin-4-yl-C(=O)-NH-CH₃ | |
| III-15 | (4) CF₃ | — | (2) (CH₃)₂N-NH-C(=O)-NH-CH₃ | |
| III-16 | (4) CF₃ | — | (2) 4-methyl-piperazin-1-yl-C(=O)-NH-CH₃ | |
| III-17 | (4) CF₃ | — | (2) (C₂H₅)₂N-NH-C(=O)-NH-CH₃ | logP = 2.70[a] |
| III-18 | (2) Cl | (4) Cl | (3) pyrrolidin-1-yl-NH-C(=O)-NH-CH₃ | logP = 1.16[a] |

TABLE 2-continued (III)

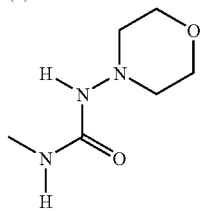

Examples of the compounds of the formula (III)

| Ex. No. | (position) R³ | (position) R⁴ | R⁵ | physical data |
|---|---|---|---|---|
| III-19 | (2) Cl | (4) Cl | (3) [morpholino-NH-C(=O)-N(CH₃)-] | logP = 1.03 ᵃ⁾ |

Starting Materials of the Formula (IIIa):

Example (IIIa-1)

[structure: methyl 2,4-dichloro-3-[[(3-methyl-2-oxo-1-imidazolidinyl)-carbonyl]-amino]-benzoate]

A mixture of 12.3 g (50 mmol) of methyl 2,4-dichloro-3-isocyanato-benzoate, 5.0 g (50 mmol) of 1-methyl-2-oxo-imidazolidine, a few drops of triethylamine and 100 ml of acetonitrile is stirred at room temperature (about 20° C.) for 18 hours and then concentrated under reduced pressure. The residue is then digested with diethyl ether and the crystalline product is isolated by filtration with suction.

This gives 11.4 g (60% of theory) of methyl 2,4-dichloro-3-[[(3-methyl-2-oxo-1-imidazolidinyl)-carbonyl]-amino]-benzoate.

log P (pH=2.3): 1.94.

Analogously to Example (III-1) it is also possible to prepare, for example, the compounds of the general formula (III) listed in Table 3 below.

TABLE 3

(IIIa)

Examples of the compounds of the formula (IIIa)

| Ex. No. | R | (position) R³ | (position) R⁴ | R⁵ | physical data |
|---|---|---|---|---|---|
| IIIa-2 | CH₃ | (2) Cl | (4) Cl | (3) N(CH₃)(OCH₃), NHC(=O)- | |
| IIIa-3 | CH₃ | (2) Cl | (4) Cl | (3) 1-(iso-C₃H₇)-2-oxo-imidazolidin-3-yl, NHC(=O)- | |
| IIIa-4 | CH₃ | (2) Cl | (4) Cl | (3) 1-methyl-2-oxo-tetrahydropyrimidin-3-yl, NHC(=O)- | |
| IIIa-5 | CH₃ | (2) Cl | (4) Cl | (3) 1-ethyl-2-oxo-imidazolidin-3-yl, NHC(=O)- | |

TABLE 3-continued
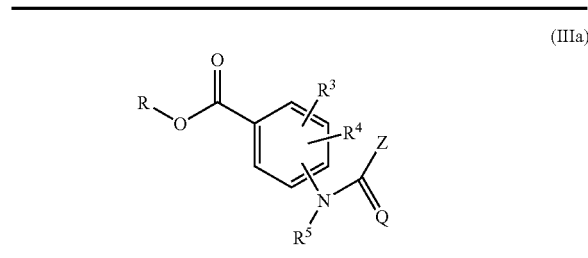
Examples of the compounds of the formula (IIIa)
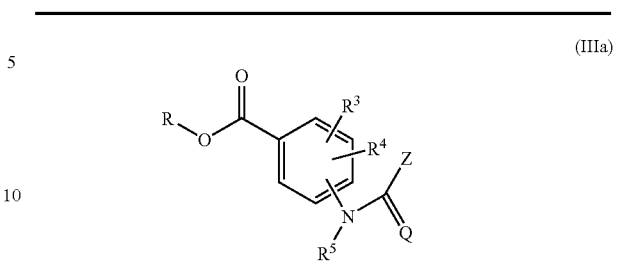
Examples of the compounds of the formula (IIIa)

TABLE 3-continued

Examples of the compounds of the formula (IIIa)

| Ex. No. | R | (position) R³ | (position) R⁴ | (position) R⁵ [—N(Z)—C(Q)=O group] | physical data |
|---|---|---|---|---|---|
| IIIa-15 | CH₃ | (4) CF₃ | — | (2) N-methylcarbamoyl-N'-dimethylhydrazide | |
| IIIa-16 | CH₃ | (4) CF₃ | — | (2) 4-methylpiperazine-1-carboxamide (N-methyl) | |
| IIIa-17 | CH₃ | (4) CF₃ | — | (2) N-methyl-N'-diethylamino-urea-type | logP = 3.10[a] |
| IIIa-18 | CH₃ | (2) Cl | (4) Cl | (3) 1,4-dimethyl-3-methylthio-1,2,4-triazol-5(4H)-one | |
| IIIa-19 | CH₃ | (2) Cl | (4) Cl | (3) 3-oxomorpholine-4-carboxamide | |
| IIIa-20 | CH₃ | (2) Cl | (4) Cl | (3) 3-(n-butyl)-2-oxotetrahydropyrimidine-1-carboxamide | logP = 3.45[a] |
| IIIa-21 | CH₃ | (2) Cl | (4) Cl | (3) 3-(iso-butyl)-2-oxotetrahydropyrimidine-1-carboxamide | logP = 3.43[a] |
| IIIa-22 | CH₃ | (2) Cl | (4) Cl | (3) 3-ethyl-2-oxotetrahydropyrimidine-1-carboxamide | |
| IIIa-23 | CH₃ | (2) Cl | (4) Cl | (3) N-methyl-N'-(pyrrolidin-1-yl)urea | logP = 1.55[a] |
| IIIa-24 | CH₃ | (2) Cl | (4) Cl | (3) N-methyl-N'-(pyrrolidin-1-yl)urea | logP = 1.80[a] |

TABLE 3-continued

Examples of the compounds of the formula (IIIa)

| Ex. No. | R | (position) R³ | (position) R⁴ | (position) R⁵ | | physical data |
|---|---|---|---|---|---|---|
| IIIa-25 | CH₃ | (2) Cl | (4) Cl | (3) | | logP = 0.93$^{a)}$ |

USE EXAMPLES

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Examples 1-1, 1-2, 1-3, 1-4, 1-5 and 1-6 exhibit strong activity against weeds, and some of them are tolerated well by crop plants, such as, for example, maize.

Example B

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3 and 4 exhibit strong activity against broad-leaved weeds and weed grasses, and they are tolerated well by crop plants.

Example C

Trial in Sown Rice (Greenhouse)

Solvent: 5 parts by weight of acetone

Emulsifier: 1 part by weight of alkylaryl polyglycol ether

To produce a suitable spray preparation, 1 part by weight of active compound is mixed with the stated amounts of solvent and emulsifier and, by mixing with water, diluted to the desired concentration.

Plant vessels (dimensions: 20 cm×20 cm×9 cm; surface: 1/200 ar) are filled with soil from a rice field. Seeds of rice and weeds are sown into the soil, which is kept moist. At the 1.5-2-leaf stage of rice, the dilute preparation of active compound is applied as a spray (foliar treatment).

One day after the treatment, the test vessels are flooded to a water depth of 3 cm. The test batches are then kept flooded (water depth 3 cm).

4 weeks after the application of active compound, the degree of damage to the plants is rated in % damage (or action against weeds) in comparison to an untreated control.

The figures denote:

0%=no effect (like untreated control)

100%=total destruction

In this test, for example, the compounds of Preparation Examples 1, 2, 3, 4, 10, 16, 23, 108 exhibit strong activity against weeds and are tolerated well by rice.

What is claimed is:

1. A compound of formula (I)

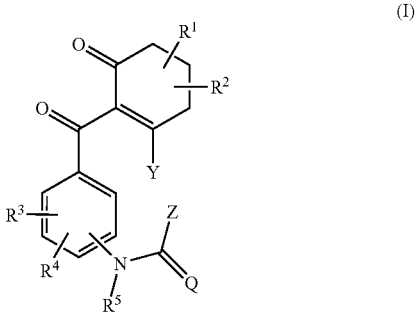

and tautomeric forms thereof or a salt of a compound of formula (I)
and tautomeric forms thereof,
in which
Q represents O (oxygen),
R¹ represents hydrogen; represents optionally fluorine- or chlorine-substituted methyl, ethyl, n- or i-propyl, methylthio, ethylthio, or n- or i-propylthio; or represents phenyl,
R² represents hydrogen; or represents optionally fluorine- or chlorine-substituted methyl, ethyl, or n- or i-propyl,
R³ represents hydrogen, nitro, cyano, fluorine, chlorine, bromine, iodine, methyl, ethyl, n- or i-propyl, difluoromethyl, trifluoromethyl, dichloromethyl, trichloromethyl, methoxy, ethoxy, difluoromethoxy, trifluoromethoxy, methylsulphonyl, or ethylsulphonyl,
R⁴ represents hydrogen, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl, or dimethylaminosulphonyl,
R⁵ represents hydrogen; or represents optionally cyano-, fluorine-, chlorine-, methoxy-, or ethoxy-substituted methyl, ethyl, n- or i-propyl, or n- or i-butyl,
Y represents hydroxyl; represents optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl, and
Z represents optionally methyl-, ethyl-, n- or i-propyl-, n-, i-, s-, or t-butyl-, difluoromethyl-, trifluoromethyl-, dichloromethyl-, trichloromethyl-, chlorodifluoromethyl-, or fluorodichloromethyl-substituted furyl, tetrahydrofuryl, furyloxy, tetrahydrofuryloxy, furylamino, tetrahydrofurylamino, furylmethyl, tetrahydrofurylmethyl, furylmethoxy, tetrahydrofurylmethoxy, furyl methylamino, tetrahydrofurylmethylamino, dioxolanyl, dioxolanylmethyl, dioxolanylmethoxy, dioxolanylmethylamino, thienyl, thienylmethyl, dithiolanyl, dithiolanylmethyl, dithiolanylmethoxy, dithiolanylmethylamino, pyrrolidinyl, pyrrolidinylamino, oxopyrrolidinyl, pyrrolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diazacyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), thiazolyl, thiazolylmethyl, dihydrothiazolyl (thiazolinyl), tetrahydrothiazolyl (thiazolidinyl), oxothiazolidinyl, cyanoiminothiazolidinyl, oxadiazolylamino, thiadiazolylamino, oxotriazolinyl, oxotetrazolinylmethyl, tetrazolylmethyl, oxotetrazolinyl, oxotetrazolinylmethyl, tetrazolylmethyl, or triazolylamino.

2. A compound of formula (I) according to claim 1 in which
R¹ and R² represent hydrogen,
R³ represents hydrogen, fluorine, chlorine, methyl, ethyl, trifluoromethyl, trichloromethyl, methoxy, ethoxy, methylsulphonyl, or ethylsulphonyl,
R⁴ represents hydrogen, fluorine, chlorine, methyl, ethyl, trifluoromethyl, trichloromethyl, methoxy, ethoxy, methylsulphonyl, or ethylsulphonyl,
R⁵ represents hydrogen, and
Y represents hydroxyl.

3. A compound of formula (I-2)

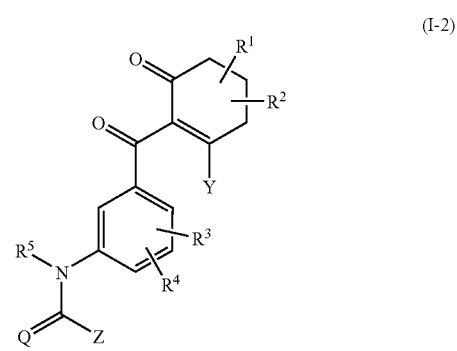

(I-2)

in which
Q represents O (oxygen),
R¹ represents hydrogen; represents optionally fluorine- or chlorine-substituted methyl, ethyl, n- or i-propyl, methylthio, ethylthio, or n- or i-propylthio; or represents phenyl,
R² represents hydrogen; or represents optionally fluorine- or chlorine-substituted methyl, ethyl, or n- or i-propyl,
R³ represents hydrogen, nitro, cyano, fluorine, chlorine, bromine, iodine, methyl, ethyl, n- or i-propyl, difluoromethyl, trifluoromethyl, dichloromethyl, trichloromethyl, methoxy, ethoxy, difluoromethoxy, trifluoromethoxy, methylsulphonyl, or ethylsulphonyl,
R⁴ represents hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinyl methyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl, or dimethylaminosulphonyl,
R⁵ represents hydrogen; or represents optionally cyano-, fluorine-, chlorine-, methoxy-, or ethoxy-substituted methyl, ethyl, n- or i-propyl, or n- or i-butyl,
Y represents hydroxyl; represents optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy, represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl, and Z represents optionally methyl-, ethyl-, n- or i-propyl-, n-, i-, s-, or t-butyl-, difluoromethyl-, trifluoromethyl-, dichloromethyl-, trichloromethyl-, chlorodifluoromethyl- or fluorodichloromethyl-substituted furyl, tetrahydrofuryl, furyloxy, tetrahydrofuryloxy, furylamino, tetrahydrofurylamino, furylmethyl, tetrahydrofurylmethyl, furylmethoxy, tetrahydrofurylmethoxy, furylmethylamino, tetrahydrofurylmethylamino, dioxolanyl, dioxolanylmethyl, dioxolanylmethoxy, dioxolanylmethylamino, thienyl, thienylmethyl, dithiolanyl, dithiolanylmethyl, dithiolanylmethoxy, dithiolanylmethylamino, pyrrolidinyl, pyrrolidinylamino, oxopyrrolidinyl, pyrrolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diaza-cyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), thiazolyl, thiazolylmethyl, dihydrothiazolyl (thiazolinyl), tetrahydrothiazolyl (thiazolidinyl), oxothiazolidinyl, cyanoiminothiazolidinyl, oxadiazolylamino, thiadiazolylamino, oxotriazolinyl, oxotetrazolinylmethyl, tetrazolylmethyl, oxotetrazolinyl, oxotetrazolinylmethyl, tetrazolylmethyl, or triazolylamino.

4. A process for preparing a compound of formula (I) according to claim 1 comprising (1) reacting a cyclohexanedione of formula (II)

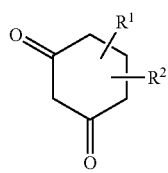

(II)

in which $R^1$ and $R^2$ have the meanings given for formula (I) in claim 1, with a substituted benzoic acid of formula (III)

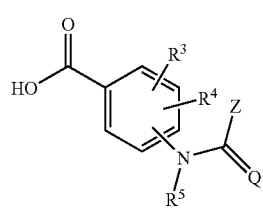

(III)

in which Q, $R^3$, $R^4$, $R^5$, and Z have the meanings given for formula (I) in claim 1, or a reactive derivative thereof, optionally in the presence of a dehydrating agent, optionally in the presence of one or more reaction auxiliaries, and optionally in the presence of one or more diluents, and (2) if appropriate, subsequently carrying out electrophilic or nucleophilic substitutions and/or oxidations or reductions on the resulting compounds of the formula (I) in a customary manner on the resulting compounds of the formula (I) to interconvert substituents within the meaning of formula (I), or converting compounds of formula (I) into salts thereof.

5. A process according to claim 4 for preparing a compound of formula (I-2)

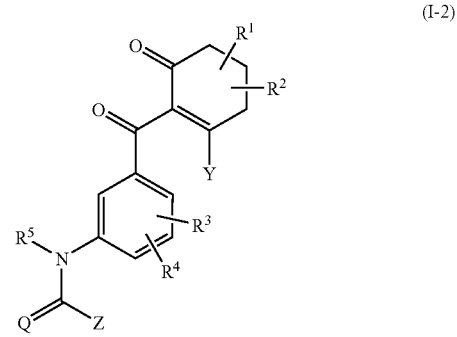

(I-2)

in which

Q represents O (oxygen), $R^1$ represents hydrogen; represents optionally fluorine- or chlorine-substituted methyl, ethyl, n- or i-propyl, methylthio, ethylthio, or n- or i-propylthio; or represents phenyl, $R^2$ represents hydrogen; or represents optionally fluorine- or chlorine-substituted methyl, ethyl, or n- or i-propyl, $R^3$ represents hydrogen, nitro, cyano, fluorine, chlorine, bromine, iodine, methyl, ethyl, n- or i-propyl, difluoromethyl, trifluoromethyl, dichloromethyl, trichloromethyl, methoxy, ethoxy, difluoromethoxy, trifluoromethoxy, methylsulphonyl, or ethylsulphonyl, $R^4$ represents hydrogen, nitro, cyano, fluorine, chlorine, bromine, iodine, methyl, ethyl, n- or i-propyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl, or dimethylaminosulphonyl, $R^5$ represents hydrogen; or represents optionally cyano-, fluorine-, chlorine-, methoxy-, or ethoxy-substituted methyl, ethyl, n- or i-propyl, or n- or i-butyl Y represents hydroxyl; represents optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyryloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl, and Z represents optionally methyl-, ethyl-, n- or i-propyl-, n-, i-, s-, or t-butyl-, difluoromethyl-, trifluoromethyl-, dichloromethyl-, trichloromethyl-, chlorodifluoromethyl-, or fluorodichloromethyl-substituted furyl, tetrahydrofuryl, furyloxy, tetrahydrofuryloxy, furylamino, tetrahydrofurylamino, furyl methyl, tetrahydrofurylmethyl, furylmethoxy, tetrahydrofurylmethoxy, furylmethylamino, tetrahydrofurylmethylamino, dioxolanyl, dioxolanylmethyl, dioxolanylmethoxy, dioxolanylmethylamino, thienyl, thienylmethyl, dithiolanyl, dithiolanylmethyl, dithiolanylmethoxy, dithiolanylmethylamino, pyrrolidinyl, pyrrolidinylamino, oxopyrrolidinyl, pyrrolyl, pyrrolylmethyl, pyrazolyl, pyrazolyloxy, pyrazolylamino, pyrazolylmethyl, imidazolyl, imidazolinyl, imidazolylmethyl, imidazolinylmethyl, oxoimidazolinyl, 2-oxo-1,3-diaza-cyclopentyl, oxazolyl, oxazolylmethyl, dihydrooxazolyl (oxazolinyl), tetrahydrooxazolyl (oxazolidinyl), isoxazolyl, dihydroisoxazolyl (isoxazolinyl), tetrahydroisoxazolyl (isoxazolidinyl), thiazolyl, thiazolylmethyl, dihydrothiazolyl (thiazolinyl), tetrahydrothiazolyl (thiazolidinyl), thiazolimino, oxothiazolidinyl, cyanoiminothiazolidinyl, oxadiazolylamino, thiadiazolylamino, oxotriazolinyl, oxotetrazolinylmethyl, tetrazolylmethyl, oxotetrazolinyl, oxotetrazolinylmethyl, or tetrazolylmethyl.

6. A herbicidal composition comprising one or more compounds of formula (I) according to claim 1 and one or more extenders.

7. A method for controlling undesirable plants comprising allowing one or more compounds according to claim 1 to act on an undesirable plant and/or its habitat.

8. A method for controlling undesirable plants comprising allowing one or more compositions according to claim 6 to act on an undesirable plant and/or its habitat.

* * * * *